(12) United States Patent
Rodriguez-Borlado et al.

(10) Patent No.: US 10,016,462 B2
(45) Date of Patent: Jul. 10, 2018

(54) ADULT CARDIAC STEM CELL POPULATION

(71) Applicant: CORETHERAPIX SLU, Madrid (ES)

(72) Inventors: Luis Rodriguez-Borlado, Madrid (ES); Itziar Palacios, Madrid (ES); José Luis Abad, Madrid (ES); Belén Sánchez, Madrid (ES); Virginia Álvarez, Madrid (ES); Rosalba Rosado, Madrid (ES)

(73) Assignee: CORETHERAPIX SLU, Madrid (ES)

( * ) Notice: Subject to any disclaimer, the term of this patent is extended or adjusted under 35 U.S.C. 154(b) by 46 days.

(21) Appl. No.: 14/775,502

(22) PCT Filed: Mar. 17, 2014

(86) PCT No.: PCT/IB2014/059904
§ 371 (c)(1),
(2) Date: Sep. 11, 2015

(87) PCT Pub. No.: WO2014/141220
PCT Pub. Date: Sep. 18, 2014

(65) Prior Publication Data
US 2016/0030485 A1 Feb. 4, 2016

(30) Foreign Application Priority Data
Mar. 15, 2013 (GB) .................................. 1304831.9

(51) Int. Cl.
*A01N 63/00* (2006.01)
*A61K 35/34* (2015.01)
(Continued)

(52) U.S. Cl.
CPC ............ *A61K 35/34* (2013.01); *C12N 5/0657* (2013.01); *C12N 5/0668* (2013.01)

(58) Field of Classification Search
None
See application file for complete search history.

(56) References Cited

U.S. PATENT DOCUMENTS

| 5,800,978 A | 9/1998 | Goodrich, Jr. et al. |
| 2004/0126879 A1 | 7/2004 | Schneider et al. |

(Continued)

FOREIGN PATENT DOCUMENTS

| EP | 2184068 A1 | 5/2010 |
| JP | 2009-527482 A | 7/2009 |

(Continued)

OTHER PUBLICATIONS

Oh et al., Proc. Nat'l. Acad. Sci. USA 100(21): 12313-12318 (2003).*

(Continued)

*Primary Examiner* — Erin M. Bowers
(74) *Attorney, Agent, or Firm* — Morrison & Foerster LLP

(57) ABSTRACT

The present invention relates to the identification, isolation, expansion and characterization of a specific type of multipotent adult cardiac stem cell. These adult stem cells are characterized in that they naturally express a specific pattern of markers, which can be used to assist with their isolation and expansion. In particular, the cells express SOX17 and GATA4, but do not express Oct4, Nanog, c-kit and telomerase reverse transcriptase. These cells are able to differentiate into one or more of the following cell types: adipocytes, osteocytes, endothelial cells and/or smooth muscle cells. They also display an unprecedented capacity for immunoregulation as well as providing, activating and/or inducing repair of damaged cardiac tissue. These adult stem cells may be used as therapeutic agents including, without limitation, for the regeneration of tissue, particularly for regeneration of damaged cardiac tissue, such as myocardium.

22 Claims, 18 Drawing Sheets

(51) Int. Cl.
*C12N 5/077* (2010.01)
*C12N 5/0775* (2010.01)

(56) References Cited

U.S. PATENT DOCUMENTS

| | | | |
|---|---|---|---|
| 2007/0020758 A1 | 1/2007 | Giacomello et al. |
| 2008/0213230 A1 | 9/2008 | Phillips et al. |
| 2008/0241111 A1 | 10/2008 | Oh et al. |
| 2011/0014161 A1 | 1/2011 | Wang et al. |
| 2011/0110897 A1 | 5/2011 | Schwarz et al. |
| 2012/0157381 A1 | 6/2012 | Spees |
| 2015/0190431 A1 | 7/2015 | Rouger et al. |

FOREIGN PATENT DOCUMENTS

| | | |
|---|---|---|
| JP | 2013-46780 A | 3/2013 |
| JP | 2013-542957 A | 11/2013 |
| WO | 2006/052925 A2 | 5/2006 |
| WO | 2008/081457 A2 | 7/2008 |
| WO | 2009/089476 A1 | 7/2009 |
| WO | 2010/007031 A2 | 1/2010 |
| WO | 2010/011352 A2 | 1/2010 |
| WO | 2010/138180 A2 | 12/2010 |
| WO | 2011/005930 A1 | 1/2011 |
| WO | 2014/141220 A1 | 9/2014 |

OTHER PUBLICATIONS

Combined Search and Examination Report received for United Kingdom Patent Application No. 1304831.9, dated Oct. 22, 2013, 8 pages.
Final Office Action received for U.S. Appl. No. 14/213,868, dated Jan. 4, 2016, 18 pages.
Non Final Office Action received for U.S. Appl. No. 14/213,868, dated Jul. 7, 2015, 13 pages.
Beltrami et al., "Multipotent Cells can be Generated in Vitro from Several Adult Human Organs (Heart, Liver, and Bone Marrow)", Blood, vol. 110, No. 9, Nov. 1, 2007, pp. 3438-3446.
Holtzinger et al., "Gata4 directs development of cardiac-inducing endoderm from ES cells", Developmental Biology, vol. 337, 2010, pp. 63-73.
Kaneda et al., "Hex is Essential for Cardiac Myogenesis in Differentiating Embryonic Stem Cells", Circulation, vol. 116, 2007, p. 104.
Koudstaal et al., "Concise Review: Heart Regeneration and the Role of Cardiac Stem Cells", Stem Cells Translational Medicine, vol. 2, 2013, pp. 434-443.
Martin et al., "Persistent Expression of the ATP-Binding Cassette Transporter, Abcg2, Identifies Cardiac SP Cells in the Developing and Adult Heart", Developmental Biology, vol. 265, 2004, pp. 262-275.
Mauritz et al., "Generation of Functional Murine Cardiac Myocytes From Induced Pluripotent Stem Cells", Circulation, vol. 118, Jul. 2008, pp. 507-517.
Niakan et al., "Sox17 Promotes Differentiation in Mouse Embryonic Stem Cells by Directly Regulating Extraembryonic Geneexpression and Indirectly Antagonizing Self-Renewal", Genes and Development, vol. 24, 2010, pp. 312-326.
International Preliminary Report on Patentability received for PCT Patent Application No. PCT/IB2014/059904, dated Apr. 29, 2015, 8 pages.
International Search Report and Written Opinion received for PCT Patent Application No. PCT/IB2014/059904, dated Jul. 8, 2014, 12 pages.
Stefanovic et al., "Interplay of Oct4 with Sox2 and Sox17: A Molecular Switch from Stem Cell Pluripotency to Specifying a Cardiac Fate", JCB Report, vol. 186, No. 5, Sep. 7, 2009, pp. 665-673.
Non Final Office Action received for U.S. Appl. No. 14/213,868, dated Oct. 17, 2016, 16 pages.
Bearzi et al., "Human Cardiac Stem Cells", PNAS, vol. 104, No. 35, Aug. 28, 2007, pp. 14068-14073.
Ferreira-Martins et al., "Cardiomyogenesis in the Developing Heart Is Regulated by C-Kit-Positive Cardiac Stem Cells", Cellular Biology, vol. 110, Mar. 2, 2012, pp. 701-715.
Yang et al., "Human Cardiovascular Progenitor Cells Develop from a KDR+ Embryonic-Stem-Cell-Derived Population", Nature, vol. 453, May 22, 2008, pp. 524-529.
Advisory Action received for U.S. Appl. No. 14/213,868, dated Oct. 4, 2017, 4 pages.
Final Office Action received for U.S. Appl. No. 14/213,868, dated Jul. 19, 2017, 15 pages.
Iida et al., "Identification of Cardiac Stem Cells with FLK1, CD31, and VE-Cadherin Expression During Embryonic Stem Cell Differentiation," The Faseb Journal, vol. 19, No. 3, Mar. 2005, pp. 371-378.
Office Action received for Japanese Patent Application No. 2015-562543, dated Jan. 30, 2018, 7 pages (3 pages of English Translation and 4 pages of Official Copy).

* cited by examiner

A)

B)

A)

B)

A)

B)

C)

SA-βGal activity

A)

B)

C)

A)

B)

A)

B)

(*) DAPI: Cardiomyocyte nuceli
(>) GFP-CSC
(▶)Fluorescent microspheres

ADULT CARDIAC STEM CELL POPULATION

CROSS REFERENCE TO RELATED APPLICATIONS

This application is a U.S. National Phase patent application of PCT/IB2014/059904, filed Mar. 17, 2014, which claims priority to United Kingdom Patent Application No. 1304831.9, filed Mar. 15, 2013, all of which are hereby incorporated by reference in the present disclosure in their entirety.

FIELD OF THE INVENTION

The present invention relates to the identification, isolation, expansion and characterization of a specific type of adult cardiac stem cell. These adult stem cells are characterised in that they naturally express a specific pattern of markers, which can be used to assist with their isolation and expansion. The cells of the invention display an unprecedented capacity for providing, activating and/or inducing repair of damaged cardiac tissue. These adult stem cells may be used as therapeutic agents including, without limitation, for the regeneration of tissue, particularly for regeneration of damaged cardiac tissue, such as myocardium.

BACKGROUND OF THE INVENTION

A number of different cardiac stem cell lines have been described in the prior art, including those described in WO 99/49015, WO 2005/012510, WO 2006/052925, WO 02/09650, WO 02/13760, WO 03/103611, WO 2007/100530, WO 2009/073616, WO 2011/057249, WO 2011/057251, WO 2012/048010, WO 2006/093276 and WO 2009/136283.

Although these stem cell lines have all been isolated by different means, they all share many of the same characteristics and may in fact be the same or substantially identical stem cell populations. In particular, the known populations of adult cardiac stem cells all share certain characteristics, markers and morphological traits. The known cells share the same origin (cardiac tissue), morphology when cultured attached to a surface, express surface markers of adult stem cells like CD90 or CD44 and most also express c-kit at some point during the expansion process, mainly when the stem cell culture is initiated. It has been also been shown that telomerase is active in these cells. In addition, all these cells have the capability to differentiate to cardiac lineages like smooth muscle, endothelial cells or cardiomyocytes.

Despite the large number of different cardiac stem cell lines are known in the prior art, there remains a need for the identification and characterisation of a cardiac stem cell line that can be used in therapeutic applications. In a therapeutic context, stem cell lines that are not genetically identical to the recipient often cause problems from immunogenic rejection of the stem cells before any therapeutic benefit can be seen. Another problem often experienced with adult-derived multipotent cells is a tendency to form teratomas upon injection into adult animals, and their use as a therapeutic is therefore limited.

There therefore remains an on-going requirement to identify a population of adult cardiac stem cells which have the potential for therapeutic use, but which do not have a propensity to form teratomas upon injection into patients. Further, there is a need for such cells that do not cause a risk of immune rejection.

SUMMARY OF THE INVENTION

The present invention provides a new population of adult cardiac stem cells that differs from the known population of cells in marker profile and morphology, and is suitable for therapeutic applications because of its low immunogenicity and inability to form teratomas when administered to an allogeneic, syngenic or immunodeficient host. The cardiac stem cells of the invention are also able to modulate the recipient's immune response to allogeneic cells and to induce angiogenesis. The cells of the present invention may be isolated from heart tissue, preferably from heart muscle tissue, and expanded in vitro attached to a surface generally used for producing cellular banks. Unlike other previously described cells, the cells of the invention are telomerase reverse transcriptase negative, so they have a limited expansion capability, which prevents tumour formation.

The cardio-protection, immunoregulatory capabilities and cardio-regenerative potential of the adult cardiac stem cells of the invention make them a suitable therapeutic tool for the treatment of different diseases such as ischemic heart disease, autoimmune diseases, wound healing processes or regenerative therapies. In particular, the following phenomena mediated by the adult cardiac stem cells of the invention make them useful therapeutic tools for the treatment of diseases in which cell death or inflammatory process are involved:

- The cardioprotective signals mediated by these cellular products will limit the loss of cells after an insult.
- The immunoregulatory capabilities of the adult cardiac stem cells will modulate the inflammatory process mediated by T cells and macrophages. Although the immune response at the initial stage after an insult is essential to remove cellular debris and initiate scar formation, a prolonged inflammatory process will not allow scar resolution and tissue regeneration.
- Finally, in vivo experiments in a rat model show the ability of the adult cardiac stem cells for inducing the formation of new tissue, reducing the scar size and increasing the presence of new muscle fibres. This will be mediated by the ability of the adult cardiac stem cells to activate endogenous stem cells.

Thus, all these activities mediated by the adult cardiac stem cells of the invention make them useful therapeutic agents for the treatment of diseases in which cell death or inflammatory process are involved. In addition, these cells could be used for promoting tissue regeneration in pathologies where new tissue formation is required. In this sense, human ischemic heart disease could be treated using these cells. The adult cardiac stem cells will limit cell loss during the acute phase of the disease, will modulate the inflammatory response to allow a faster regeneration and will finally activate endogenous tissue resident cells to promote the new tissue formation.

The Adult Cardiac Stem Cells and Adult Cardiac Stem Cell Population

The invention provides adult cardiac stem cells, particularly in the form of a substantially pure population of the adult cardiac stem cells, wherein said adult cardiac stem cells (CSCs) or the substantially pure population of adult cardiac stem cells express the markers SOX17 and GATA4, and wherein said adult cardiac stem cells or the substantially pure population of adult cardiac stem cells do not express the markers Oct4, Nanog and c-kit.

By "adult" it is meant that the stem cells are not embryonic. In one embodiment, "adult" means post-embryonic or "post-natal". With respect to the stem cells of the present invention, the term "adult stem cell" means that the stem cell is isolated from a tissue or organ of an animal at a stage of growth later than the embryonic stage. In one aspect, the stem cells of the invention may be isolated at the post-natal stage. The cells may be isolated from a mammal, such as a rat, mouse, pig or human. Adult stem cells are unlike embryonic stem cells, which are defined by their origin, the inner cell mass of the blastocyst. Adult stem cells according to the invention may be isolated from any non-embryonic tissue, and will include neonates, juveniles, adolescents and adult subjects. Generally the stem cell of the present invention will be isolated from a non-neonate mammal, and for example from a non-neonate human, rat, mouse or pig. Preferably, the stem cells of the present invention are isolated from a human, and are therefore human adult cardiac stem cells or a substantially pure population of human adult cardiac stem cells.

The adult cardiac stem cells of the invention and the substantially pure population of adult cardiac stem cells of the invention may be isolated.

The term "isolated" indicates that the cell or cell population to which it refers is not within its natural environment. The cell or cell population has been substantially separated from surrounding tissue. In some embodiments, the cell or cell population is substantially separated from surrounding tissue if the sample contains at least about 75%, in some embodiments at least about 85%, in some embodiments at least about 90%, and in some embodiments at least about 95% adult stem cells. In other words, the sample is substantially separated from the surrounding tissue if the sample contains less than about 25%, in some embodiments less than about 15%, and in some embodiments less than about 5% of materials other than the adult stem cells. Such percentage values refer to percentage by weight or by cell number. The term encompasses cells which have been removed from the organism from which they originated, and exist in culture. The term also encompasses cells which have been removed from the organism from which they originated, and subsequently re-inserted into an organism. The organism which contains the re-inserted cells may be the same organism from which the cells were removed, or it may be a different organism, i.e. a different individual of the same species.

The marker profile of the new adult cardiac stem cells and the new populations of adult cardiac stem cells can be further defined by the presence and/or absence of additional markers, or by a specific profile of a combination of present and absent markers. In each case, the specific combination of markers may be present as a particular profile within a population of cells and/or a particular profile of markers on individual cells within the population.

Thus, in one embodiment the invention provides an isolated multipotent adult cardiac stem cell, wherein said cell expresses the following markers: (a) SOX17 and GATA4, and wherein said cell does not express the following markers: (b) Oct4, Nanog, c-kit and telomerase reverse transcriptase, wherein said cell is able to differentiate into one or more of the following cell types: adipocytes, osteocytes, endothelial cells and/or smooth muscle cells. The invention also provides a substantially pure population of adult cardiac multipotent stem cells, wherein said population of cells expresses the following markers: (a) SOX17 and GATA4; and/or wherein said population does not express the following markers: (b) Oct4, Nanog, c-kit and telomerase reverse transcriptase, wherein said cell is able to differentiate into one or more of the following cell types: adipocytes, osteocytes, endothelial cells and/or smooth muscle cells.

In one specific embodiment, the adult cardiac stem cells of the invention and/or the substantially pure population of adult cardiac stem cells of the invention express one or more of SOX17 and GATA4 at a detectable level. In a further embodiment, the adult cardiac stem cells of the invention and/or the substantially pure population of adult cardiac stem cells of the invention express both SOX17 and GATA4 at a detectable level.

In one specific embodiment, at least about 95% of the adult cardiac stem cells of the invention in the substantially pure adult cardiac stem cell population of the invention express SOX17 and GATA4 at a detectable level. More specifically, at least about 95%, 96%, 97%, 98% 99% or 100% of the adult cardiac stem cells of the invention in the substantially pure adult cardiac stem cell population of the invention express SOX17 and GATA4 at a detectable level.

The adult cardiac stem cells of the invention and/or cells of the substantially pure population of adult cardiac stem cells of the invention may also express one or more, i.e. 1, 2, 3, 4, 5, 6, 7, 8, 9, 10, 11, 12, 13, 14, or all of the markers KDR, HEY2, WT1, CCL2, IL-1α, CSF3, PDGF-β, CD166, CD105, CD90, CD44, CD29, HAND2, MHC class I and/or IL8.

In one specific embodiment, the adult cardiac stem cells of the invention and/or the cells of the substantially pure population of said adult cardiac stem cells may also express IL-1β and optionally CD49c and/or HHEX. In this sense, in one specific embodiment, at least about 95% of the adult cardiac stem cells or of the cells in the substantially pure adult cardiac stem cell population of the invention express IL-1β, CD49c and HHEX at a detectable level. More specifically, at least about 95%, 96%, 97%, 98% 99% or 100% of the adult cardiac stem cells of the invention in the substantially pure adult cardiac stem cell population of the invention express IL-1β, CD49c and HHEX at a detectable level.

In one specific embodiment, the adult cardiac stem cells of the invention and/or the substantially pure population of adult cardiac stem cells of the invention express SOX17, GATA4, IL-1β, CD49c and HHEX at a detectable level and optionally one or more, i.e. 1, 2, 3, 4, 5, 6, 7, 8, 9, 10, 11, 12, 13, 14, or all of the markers KDR, HEY2, WT1, CCL2, IL-1α, CSF3, PDGF-β, CD166, CD105, CD90, CD44, CD29, HAND2, MHC class I and/or IL8 at a detectable level. In one specific embodiment, at least about 90%, 91%, 92%, 93%. 94% or 95% of the adult cardiac stem cells of the invention in the substantially pure adult cardiac stem cell population of the invention express SOX17, GATA4, IL-1β, CD49c and HHEX at a detectable level and optionally one or more, i.e. 1, 2, 3, 4, 5, 6, 7, 8, 9, 10, 11, 12, 13, 14, or all of the markers KDR, HEY2, WT1, CCL2, IL-1α, CSF3, PDGF-β, CD166, CD105, CD90, CD44, CD29, HAND2, MHC class I and/or IL8 at a detectable level. More specifically, at least about 95%, 96%, 97%, 98% 99% or 100% of the adult cardiac stem cells of the invention in the substantially pure adult cardiac stem cell population of the invention express SOX17, GATA4, IL-1β, CD49c and HHEX at a detectable level and optionally one or more, i.e. 1, 2, 3, 4, 5, 6, 7, 8, 9, 10, 11, 12, 13, 14, or all of the markers KDR, HEY2, WT1, CCL2, IL-1α, CSF3, PDGF-β, CD166, CD105, CD90, CD44, CD29, HAND2, MHC class I and/or IL8 at a detectable level.

In one embodiment, the adult cardiac stem cells of the invention and/or the substantially pure population of adult cardiac stem cells of the invention express CD31 at a detectable level. In one specific embodiment, at least about 60% (preferably at least 62%) of the adult cardiac stem cells of the invention in the substantially pure adult cardiac stem cell population of the invention express CD31 at a detectable level. Thus, in one embodiment, the adult cardiac stem cells of the invention expresses one, two or all of the following markers: (a) CD31, CD49c and/or HHEX; and/or wherein said cell does not express one, two or all of the following markers: (b) CD133, Nkx 2.5 and/or CXCR4 protein. In another embodiment, the substantially pure population of adult cardiac multipotent stem cells of the invention expresses one, two or all of the following markers: CD31, CD49c and/or HHEX; wherein said population of cells does not express two or all of the following markers: CD133, Nkx 2.5 and/or CXCR4 protein.

Thus, in one embodiment the invention provides an isolated multipotent adult cardiac stem cell, wherein said cell expresses the following markers: SOX17, GATA4, IL-1β, CD31, CD49c and HHEX; and wherein said cell does not express the following markers: Oct4, Nanog, c-kit, telomerase reverse transcriptase, CXCR4 protein, Nkx 2.5 and CD133, wherein said cell is able to differentiate into one or more of the following cell types: adipocytes, osteocytes, endothelial cells and/or smooth muscle cells. The invention also provides a substantially pure population of adult cardiac multipotent stem cells, wherein said population of cells expresses the following markers: (a) SOX17, GATA4, IL-1β, CD31, CD49c and HHEX, and wherein said cell does not express the following markers: (b) Oct4, Nanog, c-kit, telomerase reverse transcriptase, CXCR4 protein, Nkx 2.5 and CD133, wherein said cell is able to differentiate into one or more of the following cell types: adipocytes, osteocytes, endothelial cells and/or smooth muscle cells.

Preferably, the adult cardiac stem cells of the invention are isolated from heart muscle tissue.

In one specific embodiment, the adult cardiac stem cells of the invention and/or the substantially pure population of adult cardiac stem cells of the invention do not express one or more of c-kit, Oct4 and/or Nanog at a detectable level. In a further embodiment, the adult cardiac stem cells of the invention and/or the substantially pure population of adult cardiac stem cells of the invention do not express any of c-kit, Oct4 and Nanog at a detectable level.

In one specific embodiment, at least about 95% of the adult cardiac stem cells of the invention in the substantially pure adult cardiac stem cell population of the invention do not express c-kit protein at a detectable level. More specifically, at least about 95%, 96%, 97%, 98% 99% or 100% of the adult cardiac cells of the invention in the substantially pure adult cardiac stem cell population of the invention do not express c-kit protein at a detectable level.

In a further specific embodiment, at least about 95% of the adult cardiac stem cells of the invention in the substantially pure adult cardiac stem cell population of the invention do not express one or more of c-kit protein, Oct4 and/or Nanog at a detectable level. More specifically, at least about 95%, 96%, 97%, 98% 99% or 100% of the cells in the substantially pure adult cardiac stem cell population of the invention do not express one or more of c-kit protein, Oct4 and/or Nanog at a detectable level.

In a further specific embodiment, at least about 95% of the adult cardiac stem cells in the substantially pure adult cardiac stem cell population of the invention do not express any of c-kit protein, Oct4 and Nanog at a detectable level. More specifically, at least about 95%, 96%, 97%, 98% 99% or 100% of the cells in the substantially pure adult cardiac stem cell population of the invention do not express any of c-kit protein, Oct4 and Nanog at a detectable level.

In another specific embodiment, the adult cardiac stem cells of the invention and/or the substantially pure population of adult cardiac stem cells of the invention may also not express one or more of Nkx 2.5, CXCR4 protein and/or CD133 at a detectable level. In a further embodiment, the adult cardiac stem cells of the invention and/or the substantially pure population of adult cardiac stem cells of the invention do not express any of Nkx 2.5, CXCR4 protein and CD133 at a detectable level.

In a further specific embodiment, at least about 95% of the adult cardiac stem cells of the invention and/or of the cells in the substantially pure adult cardiac stem cell population of the invention do not express one or more of Nkx 2.5, CXCR4 protein and/or CD133 at a detectable level. More specifically, at least about 95%, 96%, 97%, 98% 99% or 100% of the adult cardiac stem cells in the substantially pure adult cardiac stem cell population of the invention do not express one or more of Nkx 2.5, CXCR4 protein and/or CD133 at a detectable level. The adult cardiac stem cells of the invention and/or cells of the substantially pure population of adult cardiac stem cells of the invention may also not express one or more, i.e. 1, 2, 3, 4, 5, 6, or all of the markers CD45, CD34, CD11b, telomerase reverse transcriptase, CD40, CD80, and/or CD86.

In one specific embodiment, the adult cardiac stem cells of the invention and/or cells of the substantially pure population of adult cardiac stem cells of the invention express the combination of the markers SOX17 and GATA4, and do not express the combination of the markers Oct4, Nanog and c-kit. In one specific embodiment, at least about 95%, for example least about 95%, 96%, 97%, 98% 99% or 100%, of the adult cardiac stem cells in the substantially pure population of adult cardiac stem cells of the invention express the combination of the markers SOX17 and GATA4, and do not express the combination of the markers Oct4, Nanog and c-kit.

In one specific embodiment, the adult cardiac stem cells of the invention and/or cells of the substantially pure population of adult cardiac stem cells of the invention express the combination of the markers SOX17, GATA4, IL-1β, CD49c and HHEX, and do not express the combination of the markers Oct4, Nanog, c-kit, Nkx 2.5, CXCR4 protein, telomerase reverse transcriptase and CD133. In one specific embodiment, at least about 95%, for example at least about 95%, 96%, 97%, 98% 99% or 100%, of the adult cardiac stem cells of the invention and/or cells of the substantially pure population of adult cardiac stem cells of the invention express the combination of the markers SOX17, GATA4, IL-1β, CD49c and HHEX, and do not express the combination of the markers Oct4, Nanog, c-kit, Nkx 2.5, CXCR4 protein, telomerase reverse transcriptase and CD133.

In one specific embodiment, the adult cardiac stem cells of the invention and/or the substantially pure population of adult cardiac stem cells of the invention express the combination of the markers SOX17, GATA4, IL-1β, CD49c and HHEX and optionally one or more, i.e. 1, 2, 3, 4, 5, 6, 7, 8, 9, 10, 11, 12, 13, 14, or all of the markers KDR, HEY2, WT1, CCL2, IL-1α, CSF3, PDGF-β, CD166, CD105, CD90, CD44, CD29, HAND2, MHC class I and/or IL8 at a detectable level, and do not express the combination of the markers Oct4, Nanog, c-kit, Nkx 2.5, CXCR4 protein, telomerase reverse transcriptase and CD133 and optionally CD45, CD34, CD11b, telomerase reverse transcriptase, CD40, CD80, and/or CD86 at a detectable level. In a further specific embodiment, at least about 95%, for example least about 95%, 96%, 97%, 98% 99% or 100%, of the adult cardiac stem cells of the invention and/or the substantially pure population of adult cardiac stem cells of the invention express the combination of the markers SOX17, GATA4, IL-1β, CD49c and HHEX and optionally one or more, i.e. 1, 2, 3, 4, 5, 6, 7, 8, 9, 10, 11, 12, 13, or all of the markers KDR, HEY2, WT1, CCL2, IL-1α, CSF3, PDGF-β, CD166, CD105, CD90, CD44, CD29, HAND2, MHC class I and/or IL8 at a detectable level, and do not express the combination of the markers Oct4, Nanog, c-kit, Nkx 2.5, CXCR4 protein, telomerase reverse transcriptase and CD133 and optionally CD45, CD34, CD11b, telomerase reverse transcriptase, CD40, CD80, and/or CD86 at a detectable level.

In certain specific embodiments, the adult cardiac stem cells of the invention and/or the substantially pure population of adult cardiac stem cells of the invention express all of the markers SOX17, GATA4, WT1, HEY2 and KDR. In a further specific embodiment, the adult cardiac stem cells of the invention and/or the substantially pure population of adult cardiac stem cells of the invention express all of the markers SOX17, GATA4, CD44, CD90, CD105, CD166, WT1, HEY2 and KDR. Preferably, the adult cardiac stem cells of the invention and/or the substantially pure population of adult cardiac stem cells of the invention express the following markers: CD31, IL-1β, CD44, CD90, CD105, CD166, WT1, HEY2, KDR, CCL2, IL-1α, CSF3, PDGF-b, CD29, HAND2, MHC class I and/or IL-8; and do not express the following markers: CD45, CXCR4 protein, Nkx 2.5, CD34, CD11b, CD40, CD80 and/or CD86.

In a further specific embodiment, the adult cardiac stem cells of the invention and/or the substantially pure population of adult cardiac stem cells of the invention do not express any of the markers Oct4, Nanog, c-kit, CD40, CD80 and CD86. In a yet further embodiment, the adult cardiac stem cells of the invention and/or the substantially pure population of adult cardiac stem cells of the invention do not express any of the markers Oct4, nanog, c-kit, CD45, and telomerase reverse transcriptase.

In certain embodiments of the invention, the adult cardiac stem cells of the invention and/or the substantially pure population of adult cardiac stem cells have the following marker expression profile: SOX17, GATA4, CD44, CD90, CD105, CD166, WT1 and KDR positive, and Oct4, Nanog, c-kit, CD45, and telomerase reverse transcriptase negative.

The invention also provides a "mixed population of cells" comprising at least about 0.5% (in other aspects at least 1%, 5%, 10%, 20%, 30%, 40%, 50%, 60% or 70%) of the adult CSCs of the invention cells other than the adult CSCs of the invention such as, but not limited to, MSCs from adipose tissue or from bone marrow, epicardial cells, endothelial cells, pericytes and fibroblasts. Preferably, the mixed population of cells comprises MSCs. More preferably, at least about 80% (in other aspects at least 85%, 90%, 91%, 92%, 93%, 94%, 95%, 96%, 97%, 98%, 99% or 99.5%) of the cells of the mixed population of cells are MSCs.

By "substantially pure" in reference to the substantially pure population of cells of the invention, it is meant a population of stem cells, wherein the cell population essentially comprises only adult cardiac stem cells of the invention, i.e. the cell population is substantially pure. In many aspects of the invention, the cell population comprises at least about 80% (in other aspects at least 85%, 90%, 91%, 92%, 93%, 94%, 95%, 96%, 97%, 98%, 99%, 99.5%, 99.9% or 100%) of the adult cardiac stem cells of the invention.

The term "marker" as used herein encompasses any biological molecule whose presence, concentration, activity, or phosphorylation state may be detected and used to identify the phenotype of a cell.

The term "expressed" is used to describe the presence of a marker within a cell. In order to be considered as being expressed, a marker must be present at a detectable level. By "detectable level" is meant that the marker can be detected using one of the standard laboratory methodologies such as PCR, blotting, immunofluorescence, ELISA or FACS analysis. "Expressed" may refer to, but is not limited to, the detectable presence of a protein, phosphorylation state of a protein or an mRNA encoding a protein. A gene is considered to be expressed by a cell of the invention or a cell of the population of the invention if expression can be reasonably detected after 30 PCR cycles, preferably after 37 PCR cycles, which corresponds to an expression level in the cell of at least about 100 copies per cell. The terms "express" and "expression" have corresponding meanings. At an expression level below this threshold, a marker is considered not to be expressed. The comparison between the expression level of a marker in an adult stem cell of the invention, and the expression level of the same marker in another cell, such as for example a mesenchymal stem cell, may be conducted by comparing the two cell types that have been isolated from the same species. Preferably this species is a mammal, and more preferably this species is human. Such comparison may conveniently be conducted using a reverse transcriptase polymerase chain reaction (RT-PCR) experiment.

The adult cardiac stem cells of the invention and/or the population of adult cardiac stem cells of the invention are characterized in that they have a distinctive expression level for certain markers. It is shown herein that the adult cardiac stem cells of the invention and/or the adult cardiac stem cell population of the invention express many specific markers at a detectable level.

The adult cardiac stem cell populations of the invention are considered to express a marker if at least about 80% of the cells of the invention in the population show detectable expression of the marker. In other aspects, at least about 85%, at least about 90% or at least about 95% or at least about 97% or at least about 98% or more of the cells of the invention in the populations show detectable expression of the marker. In certain aspects, at least about 99% or 100% of the cells of the invention in the population show detectable expression of the markers. Expression may be detected through the use of any suitable means such as an RT-PCR experiment, immunoblotting, immunofluorescence, ELISA or through fluorescence activated cell sorting (FACS). It should be appreciated that this list is provided by way of example only, and is not intended to be limiting.

In an alternative embodiment, the adult cardiac stem cells of the invention and/or the substantially pure population of adult cardiac stem cells of the invention are considered to express a marker if the expression level of the marker is greater in the cells of the invention than in a control cell, for example in mesenchymal stem cells. By "greater than" in this context, it is meant that the level of the marker expression in the cell population of the invention is at least 2-, 3-, 4-, 5-, 10-, 15-, 20-fold higher than the level in the control cell.

In one specific embodiment, level of mRNA transcript of SOX 17 and GATA4 in the adult cardiac stem cells of the invention and/or the substantially pure population of adult cardiac stem cell of the invention is at least about 10 times greater, e.g. about 10 times greater, about 15 times greater or about 20 times or more greater, than the corresponding level of the same mRNA transcripts than mesenchymal stem cells obtained from bone marrow or from adipose tissue.

In one specific embodiment, the level of mRNA transcript of WT1, HEY2 and/or KDR in the adult cardiac stem cells of the invention and/or the substantially pure population of adult cardiac stem cell of the invention is at least about 10 times greater, e.g. about 10 times greater, about 15 times greater or about 20 times or more greater, than the corresponding level of the same mRNA transcripts than mesenchymal stem cells obtained from adipose tissue.

In a further specific embodiment, the level of mRNA transcript of IL-1α, Colony Stimulating Factor 3 (CSF3) and/or PDGF-β in the adult cardiac stem cells of the invention and/or the substantially pure adult population of cardiac stem cell of the invention is at least about five times greater, for example about 5 times greater, about 10 times greater or about 15 times or more greater, than the corresponding level of the same mRNA transcripts than mesenchymal stem cells obtained from adipose tissue.

The adult cardiac stem cells of the invention and/or the substantially pure population of adult cardiac stem cell population of the invention may also be characterised in that the adult cardiac stem cells of the invention and/or the substantially pure population of adult cardiac stem cell population of the invention do not express a particular marker or combination or markers at a detectable level. Many of these are indicative of a differentiated or partially differentiated cell. As defined herein, these markers are said be to be negative markers.

In some embodiments, the substantially pure adult cardiac stem cell population of the invention is considered not to express a marker if at least about 80% of the adult cardiac stem cells present therein do not show detectable expression of the marker. In other embodiments, at least about 85%, at least about 90% or at least about 95% or at least about 97% or at least about 98% or at least about 99% or 100% of the adult cardiac cells present therein do not show any detectable expression of the marker. Again, lack of detectable expression may be proven through the use of an RT-PCR experiment, immunoblotting, immunofluorescence, ELISA or using FACS.

The markers described herein are considered not to be expressed by an adult cardiac stem cell of the invention, if expression cannot be reasonably detected at a level of 30 cycles of PCR, which corresponds to an expression level in the cell of less than about 100 copies per cell and/or cannot be readily detected by immunofluorescence, immunoblotting, ELISA or FACS.

Specific Markers of the Invention

The markers referred to in the present invention include the specific reference sequence for that marker, and any known orthologs of those markers. The markers include SOX17, GATA4, KDR, WT1, CCL2, IL-1α, IL-8, IL6, G-CSF, CXCL1, sICAM-1, CSF3, PDGF-β, CD166, CD105, CD90, CD44, CD29, HAND2, MHC class I, CD45, CD34, CD11b, telomerase reverse transcriptase, CD40, CD80, CD86, CD31, IL-1β, CD49c, HHEX, CXCR4 protein, Nkx 2.5 and CD133.

The term Nanog includes Nanog and any orthologs thereof, including but not limited to 2410002E02Rik, ENK, ecat4 homeobox transcription factor Nanog, and homeobox transcription factor Nanog-delta 48.

The term Oct-4 includes Oct-4 and any orthologs thereof, including but not limited to Pou5f1, POU domain class 5 transcription factor 1, Oct-3, Oct-3/4, Oct3, Otf-3, Otf-4, Otf3-rs7, and Otf3g.

The term c-kit includes c-kit and any orthologs thereof, included but not limited to CD117, Fdc, Gsfsco1, Gsfsco5, Gsfsow3, SCO1, SCO5, SOW3, Ssm, Tr-kit, and KIT.

The term TERT includes TERT and any orthologs thereof, including but not limited to telomerase reverse transcriptase, EST2, TCS1, TP2, TRT, hEST2, and telomerase catalytic subunit.

The term SOX17 includes Sox17 and any orthologs thereof, including but not limited to NG_028171.1 GI:325053743.

The term CD90 includes CD90 and any orthologs thereof, including but not limited to Thy1, thymus cell antigen 1, theta, T25, Thy-1, Thy-1.2, Thy1.1, and Thy1.2.

The term CD166 includes CD166 and any orthologs thereof, including but not limited to Alcam, activated leukocyte cell adhesion molecule, AI853494, BEN, DM-GRASP, MGC27910, MuSC, and SC1.

The term cd11b includes cd11b and any orthologs thereof, including but not limited to Itgam, integrin alpha M, CD11b/CD18, CR3, CR3A, F730045J24Rik, Ly-40, MAC1, Mac-1, Mac-1a, CD11B (p170); Mac-1 alpha; cell surface glycoprotein MAC-1 alpha subunit; complement component receptor 3 alpha, complement component receptor 3 alpha-a, complement receptor type 3, leukocyte adhesion receptor MOL and macrophage antigen alpha.

The term CD29 includes CD29 and any orthologs thereof, including but not limited to ITGB1, integrin, beta 1 fibronectin receptor, beta polypeptide, MDF2, MSK12, FNRB, GPIIA, MDF2, MSK12, VLAB, OTTHUMP00000046253, OTTHUMP00000063731, OTTHUMP00000063732; OTTHUMP00000063733, fibronectin receptor beta subunit, integrin VLA-4 beta subunit, and integrin beta 1.

The term CD105 includes CD105 and any orthologs thereof, including but not limited to ENG, endoglin, RP11-228B15.2, END, FLJ41744, HHT1, ORW, and ORW1.

The term Gata-4 includes Gata-4 and any orthologs thereof, including but not limited to GATA-4 zinc-finger transcription factor.

The term CD31 includes CD31 and any orthologs thereof, CD31 including but not limited to PECAM1, platelet/endothelial cell adhesion molecule, CD31/EndoCAM, PECAM-1, and CD31/EndoCAM adhesion molecule.

The term IL-1β includes IL-1b and any orthologs thereof, including but not limited to IL-1β, IL1-BETA, IL1F2, and catabolin The term CD49c includes CD49c and any orthologs thereof, including but not limited to ITGA3, GAP-B3, VCA-2, VLA3a, antigen identified by monoclonal antibody J143, and MSK18

The term HHEX includes HHEX and any orthologs thereof, including but not limited to HEX, HOX11L-PEN, and PRHX The term CXCR4 protein includes CXCR4 protein and any orthologs thereof, including but not limited to fusin or CD184, D2S201E, FB22, HM89, HSY3RR, LAP3, LCR1, LESTR, NPY3R, NPYR, NPYRL, NPYY3R, and WHIM The term Nkx 2.5 includes Nkx 2.5 and any orthologs thereof, including but not limited to CHNG5, cardiac-specific homeo box, CSX, CSX1, HLHS2, NKX2-5, NKX2E, NKX4-1, and VSD3

The term CD133 includes CD133 and any orthologs thereof, including but not limited to prominin 1, PROM1, MCDR2, STGD4, CORD12, RP41, AC133, MSTP061, PROMLI, hProminin, hematopoietic stem cell antigen, and prominin-like 1.

Cellular Morphology and Other Characteristics

The population of adult cardiac stem cells of the present invention is made up of cells that possess distinctive morphology. Typically, cardiosphere derived cells known in the prior art are at least 20 µm in diameter. However, the adult cardiac stem cells of the present invention are typically smaller and have a diameter of less than about 20 µm. In a specific embodiment, the average diameter of the adult cardiac stem cells of the invention in the substantially pure population of adult cardiac stem cells of the present invention or in the mixed population of cells of the present invention is ≤18 µm, ≤17 µm, ≤16 µm, ≤15 µm, ≤14 µm or even less. In a specific embodiment, the average diameter of the adult cardiac stem cells of the invention in the substantially pure population of adult cardiac stem cells of the present invention or in the mixed population of cells of the present invention is in the rage of ≥ about 10 µm to ≤ about 15 µm. In a further embodiment, the diameter of at least 90%, for example at least 95%, at least 96%, at least 97%, at least 98%, at least 99% or more, of the adult cardiac stem cells of the invention in the substantially pure population of adult cardiac stem cells of the present invention or in the mixed population of cells of the present invention is in the range of ≥ about 10 µm to ≤ about 15 µm.

The morphology of the adult cardiac stem cells of the present invention makes the population of cells particularly useful in therapeutic applications because their relatively small size makes them more suitable for administration to coronary, and other, blood vessels. For example, the substantially pure adult cardiac stem cell population of the present invention is particularly well suited for administration to coronary arteries, coronary veins, and/or directly to the myocardium. The substantially pure adult cardiac stem cell population of the present invention is well suited to administration by injection or via a catheter.

The adult cardiac stem cells of the present invention possess clonogenic capacity, i.e. the cells are able to form clones. The term "clonogenic" relates to the clonal proliferation capacity of the cells of the invention. The term is intended to convey that single cells after seeded are able to proliferate and to recapitulate the original culture.

In some embodiments, the substantially pure adult stem cell population of the invention is considered to have clonogenic capabilities if at least about 10% of the adult cardiac stem cells proliferate and establish a cell culture after seeding as single cells. In some embodiments at least about 15%, in some embodiments at least about 20%, in some embodiments at least about 25%, and in some embodiments at least 30% or more of the adult cardiac stem cells of the invention of the substantially pure population of adult cardiac stem cells or of the mixed population of cells of the invention have clonogenic capabilities.

The adult cardiac stem cells of the invention in the substantially pure adult stem cell population or in the mixed population of cells of the invention are also capable of self-renewal. That is, the adult cardiac stem cells of the invention give rise to daughter cells with the same characteristic pattern of marker expression and development potential as the mother cell. This characteristic can be determined through the capacity of a culture of the cells on the invention to undergo multiple passages without losing the pattern of marker expression. However, the adult cardiac stem cells of the invention cannot be passaged indefinitely. The adult stem cells of the present invention can be duplicated up to 20 times without any change in characteristics. In one embodiment, the adult stem cells of the present invention can be duplicated up to 50 times without any change in characteristics.

The adult cardiac stem cells of the invention in the substantially pure adult stem cell population of the invention or in the mixed population of cells of the invention also exhibit a high degree of genomic stability. By a "high degree of genomic stability" it is meant that the substantially pure adult stem cell population of the invention can be passaged up to 5 times, expanded and/or administered to a subject without any evidence of chromosomal alterations using comparative Genome Hybridization analysis. In a specific embodiment, ≤ about 25%, e.g. ≤ about 20%, ≤ about 15%, ≤ about 10% or less, of the cells in the substantially pure adult stem cell population of the invention exhibit any chromosomal alterations. The term "chromosomal alterations" includes any rearrangement of the chromosomal structure, which allows the chromosomal structure to differ from the normal, expected chromosomal structure. By way of example, the term encompasses chromosome translocation, chromosomal breakage and chromosome multiplication or loss.

The adult cardiac stem cells of the present invention are capable of forming cardiospheres when cultured in suspension. The term "cardiosphere" is well known in the art and includes pseudo-embryoid bodies made up of a clone of cardiac stem cells. An "embryoid body" or a "pseudo-embryoid body", which in this application are used as synonyms, is an aggregate of cells that under the culture conditions given in the application start to differentiate into different cell types.

In certain embodiments, the adult cardiac stem cells of the invention in the substantially pure adult stem cell population or in the mixed population of cells of the invention are considered to be capable of forming pseudo embryoid bodies if at least about 20% of the adult cardiac stem cells of the invention in the substantially pure adult stem cell population or in the mixed population of cells of the invention are capable of forming pseudo embryoid bodies. In some embodiments, at least about 25%, at least about 30% or at least about 35% or more of the adult cardiac stem cells of the invention in the substantially pure adult stem cell population or in the mixed population of cells of the invention are capable of forming embryoid bodies.

Conventionally, such pseudo embryoid bodies are produced by the hanging drop method. However, the cells of the invention form embryoid bodies readily when cultured in growth medium in bacterial culture dishes which are not coated with negative charge. It will be clear to a person skilled in the art that this definition is not intended to be limiting, and that any method known in the art for the production of embryoid bodies may be used. The ability of the cells of the invention to form pseudo embryoid bodies when plated at low density in ultra-low adherent dishes is a characteristic of their ability to self-renew which can be exploited for their isolation and separation from the other cells present in cultures from the same tissue which are not adult cardiac stem cells of the invention. The adult cardiac stem cells of the present invention are also able to induce monocyte migration and/or monocyte recruitment in a cell migration assay. A preferred cell migration assay is described in Example 3D. By "able to induce monocyte migration or recruitment" it is meant culture medium previously used for growing the adult stem cells of the present invention, when placed in the lower chamber in a cell migration assay as described herein, induces monocytes placed in an upper chamber to migrate through 5 microns membrane pores to the lower chamber at a rate that is at least 1.5, 2, 3, 4, 5 or more times greater than the rate induced by culture medium previously used for growing mesenchymal stem cells (MSC).

The adult cardiac stem cells of the present invention are also able to induce monocyte proliferation. By "induce monocyte proliferation" it is meant that co-culture of a substantially pure population of adult cardiac stem cells of the invention with monocytes causes the monocytes to proliferate at least 2, 3, 4, 5, 10, 15, 20 or more times faster than the basal rate of proliferation of the monocytes alone or monocytes in a co-culture with MSC. Monocyte proliferation can be measured by any method described herein or known in the art.

The ability to induce monocyte recruitment, migration and/or proliferation may be important for the therapeutic applications of the adult cardiac stem cells of the present invention. While not wishing to be bound by theory, the inventors believe that after administration to a subject, the adult cardiac stem cells of the present invention induce monocyte recruitment and proliferation. The monocytes in turn perform a role in modulating the subject's immune response. The presence of monocytes may also induce angiogenesis in the subject.

The adult cardiac stem cells of the present invention are also able to modulate a T lymphocyte response. Modulation of the T lymphocyte response can be measured by any assay known in the art or described herein. A preferred assay is given in Example 3E. By "modulate a T lymphocyte response" it is meant that the adult cardiac stem cells of the present invention are able to modulate activated T-cell proliferation and in particular are able to activate and expand regulatory T cell populations and/or down-regulate proliferation of $CD4^+$ and $CD8^+$ T-cells. In a particular embodiment, co-culture of a suspension comprising a substantially pure population of adult cardiac stem cells of the invention with regulatory T cells increases the proportion of proliferative regulatory T cells by 10%, 20%, 30%, 40%, 50%, 60%, 70%, 80%, 90%, 100%, 150%, 200% or more compared to regulatory T cells cultured alone. In another particular embodiment, co-culture of a suspension comprising a substantially pure population of adult cardiac stem cells of the invention with PHA-activated T cells decreases the proliferation of the $CD4^+$ and $CD8^+$ T-cells by 10%, 20%, 30%, 40%, 50%, 60%, 70%, 80%, 90% or more compared to PHA-activated T cells cultured alone. In another embodiment, the number of duplications of human primary T lymphocytes activated with IL2 plus CD3/CD28 Dynabeads is reduced when co-cultured with Mitomycin C treated adult cardiac stem cells of the invention by 10%, 20%, 30%, 40%, 50%, 60%, 70%, 80%, 90% or more compared to a negative control without adult cardiac stem cells of the invention.

These T lymphocyte regulatory properties may contribute to the low immunogenicity of the adult cardiac stem cells of the invention and thus of the substantially pure population of adult cardiac stem cells of the invention or the mixed population of cells of the invention, which in turn makes them suitable to use in therapy and suitable for administration as allogeneic cells. The adult cardiac stem cells of the present invention display a weak immunogenic profile. The adult cardiac stem cells of the invention in the substantially pure adult cardiac stem cell population of the present invention or in the mixed population of cells of the invention do not express the markers CD40, CD80, and/or CD86. The low immunogenicity and weak immunogenic profile of the adult cardiac stem cells of the present invention allows the cells to avoid acute rejection by the recipient's immune system, thus preventing and/or delaying elimination from the recipient. The adult cardiac stem cells of the present invention thus remain in the recipient for an amount of time sufficient for a therapeutic benefit to occur. The ability to modulate the immune response of the recipient is also useful in therapeutic applications because it contributes to the ability of the adult cardiac stem cells of the present invention to prevent scar formation in damaged tissue and to promote myocardial regeneration.

The adult cardiac stem cells of the invention either do not trigger an immune response in vitro or in vivo or trigger an immune response which is substantially weaker than that which would be expected to be triggered upon injection of an allogeneic cell population into a subject. In certain aspects of the invention, the adult cardiac stem cells and/or the substantially pure adult cardiac stem cell population is considered not to trigger an immune response if at least about 70% of the cells of the adult cardiac stem cells and/or the substantially pure adult cardiac stem cell population do not trigger an immune response. In some embodiments, at least about 80%, at least about 90% or at least about 95%, at least about 99% or more of the cells of the substantially pure adult cardiac stem cell population do not trigger an immune response or trigger only a weak immune response. Preferably the cells of the invention do not trigger an antibody mediated immune response or do not trigger an in vivo humoral immune response, or trigger a weaker response than that which would be expected to be triggered upon injection of an allogeneic cell.

By "weak immune response" it is meant that the immune response triggered by the adult cardiac stem cells of the invention and/or the substantially pure population of adult cardiac stem cells of the invention is less than about at 40%, ≤ about 30%, ≤ about 25%, ≤ about 20% or ≤ about 10% or less of the level of a corresponding immune response triggered by a control allogeneic cell or population of cells.

The lack of immune response, or the presence of a weak immune response, can be assessed using any conventional means and as described herein in the Examples, preferably as described in Example 4A. In one embodiment, the adult cardiac stem cells and/or the substantially pure population of adult cardiac stem cell of the invention will be considered not to trigger an immune response or to trigger only a weak immune response if the level of allogeneic antibodies against the injected cells of the invention is less than 10% of the level of allogeneic antibodies against injected control cells such as MSCs or terminally differentiated cells from a non-matched individual. Specifically, the level of allogeneic antibodies against the injected cells of the invention is ≤ about 9%, ≤ about 8%, ≤ about 7%, ≤ about 6%, ≤ about 5%, ≤ about 4%, ≤ about 3%, ≤ about 2%, ≤ about 1%, ≤ about 0.5% or less of the level of allogeneic antibodies against injected control cells such as MSCs or terminally differentiated cells from a non-matched individual.

In a particularly preferred embodiment, the level of allogeneic antibodies against the injected cells or population of cells of the invention is not detectable by conventional means such as flow cytometry.

In one embodiment, the adult cardiac stem cells and/or the substantially pure adult cardiac stem cell population of the invention will be considered not to trigger an immune response or to trigger only a weak immune response if the level of expression of one or more of IL2, IFNλ, TNFβ, IL4, IL5, IL10, IL3, TNFα and/or TGFβ, induced following incubation of the substantially pure adult cardiac stem cell population with T cells from an unmatched individual, is less than about 50% of the level of expression of one or more of IL2, IFNλ, TNFβ, IL4, IL5, IL10, IL3, TNFα and/or TGFβ following incubation of an equivalent T cell population with terminally differentiated cells or MSCs isolated from a non-matched individual. In some embodiments, the level of expression of one or more of IL2, IFNλ, TNFβ, IL4, IL5, IL10, IL3, TNFα and/or TGFβ induced following incubation of the substantially pure adult cardiac stem cell population with T cells from an unmatched individual is less than about 40%, about 30%, about 25%, about 20% or about 10% or less of the level of expression of one or more of IL2, IFNλ, TNFβ, IL4, IL5, IL10, IL3, TNFα and/or TGFβ following incubation of an equivalent T cell population with terminally differentiated cells or MSCs isolated from a non-matched individual. In a specific embodiment, the level of both IL2 and IFNλ induced following incubation of the substantially pure adult cardiac stem cell population with T cells from an unmatched individual is less than about 50% (e.g. ≤ about 40%, ≤ about 30%, ≤ about 25%, ≤ about 20% or ≤ about 10% or less) of the level of expression of both IL2 and IFNλ induced following incubation of terminally differentiated cells with equivalent T cells from an unmatched individual.

In another embodiment, the consequent immune response produced by the assay described above may be measured by detecting the proliferation rate of the T cells in the assay. In one embodiment, the substantially pure adult cardiac stem cell population of the invention will be considered not to trigger an immune response if the proliferation rate of T cells from an unmatched individual, following incubation with the substantially pure adult cardiac stem cell population, is less than about 50% of the doubling rate of an equivalent population of T following incubation with terminally differentiated cells or PBMCs isolated from a non-matched individual. In some embodiments, the proliferation rate induced following incubation of the isolated adult stem cells with T cells from an unmatched individual is less than about at 40%, about 30%, about 25%, about 20% or about 10% or less of the T cell doubling rate following incubation of an equivalent T cell population with terminally differentiated cells isolated from a non-matched individual.

The assays described above are provided by way of illustration only, and are not intended to be exhaustive. The skilled person will be aware of various alternative assays which might be used. Preferred assays are described herein in the Examples.

The adult cardiac stem cells of the present invention are also able to secrete anti-apoptotic factors. Secretion of anti-apoptotic factors can be measures as described herein, and in particular as described in Example 3F. In certain embodiments, the secretion of anti-apoptotic factors can be measured by comparing cell viability of insulted cardiomyocytes that are exposed either to the culture medium used for the expansion of a substantially pure population of adult cardiac stem cells of the invention or to the culture medium used for the expansion of MCS. In a particular embodiment, the cell viability of cells exposed to the substantially pure population of adult cardiac stem cells of the invention is at least 2, 3, 4, 5, 10 or more times greater than the control.

The adult cardiac stem cells of the present invention are also capable of promoting cardio-regeneration, for example by inducing regeneration of endogenous cardiomyocytes, promoting new muscle formation and/or preventing scar formation and remodeling of cardiac tissues. A preferred assay for measuring the promotion of cardio-regeneration is given in Example 4C.

The adult cardiac stem cells present in the substantially pure population of adult cardiac stem cells of the invention or in the mixed population of cells of the invention are also multipotent. By "multipotent" it is meant that the stem cell is capable of generating cell types from multiple lineages, but only a limited number of lineages.

In particular, the cells in the substantially pure population of adult cardiac stem cells of the invention or in the mixed population of cells of the invention are able to differentiate into one or more of the following cell types: adipocytes, osteocytes, endothelial cells, cardiomyocytes and/or smooth muscle cells.

Methods of Generating the Population of Adult Cardiac Stem Cells of the Invention Many methods are known in the art for the preparation of cardiac stem cells from cardiac tissue. The present invention provides a method of preparing adult cardiac stem cells and/or a substantially pure population of adult cardiac stem cells according to the present invention. Having identified a number of markers that are unique to the desired population of adult cardiac stem cells, the inventors have developed a method of preparing said population comprising the steps of:
(a) providing a suspension comprising a population of adult cardiac stem cells; and
(b) selecting cells that express at least SOX17 and GATA 4.

The selection may be carried out by detecting the expression of at least SOX17 and GATA 4 by any conventional means, and discarding cells that do not express these markers. In a particular embodiment, a cell pellet is obtained after step (a) and cells expressing high levels of mRNA for SOX17 and GATA4 are selected for further processing.

The methods of the invention may further comprise the step, step (c), of expanding the cells that are selected in step (b). In this embodiment, the invention provides a method of preparing a substantially pure population of cardiac stem cells according to the invention, comprising the steps of:
(a) providing a suspension comprising a population of adult cardiac stem cells;
(b) selecting cells that express at least SOX17 and GATA 4; and
(c) expanding the cells that are selected in step (b).

This expansion step provides a substantially pure population of adult cardiac stem cells comprising a larger number of cells. The expansion step is therefore useful in increasing the size of the population of cells of the invention that are available for downstream uses such as therapeutic applications described herein.

The methods of the of the invention may further comprise the step, step (d), of confirming that the substantially pure population of stem cells that results from the expansion step (c) still express at least SOX17 and GATA 4. Thus, the methods of the invention may comprise the step of confirming the expression of at least SOX17 and GATA 4 in the expanded cells from step (c). In this embodiment, the invention provides a method of preparing a substantially pure population of cardiac stem cells according to the invention, comprising the steps of:
(a) providing a suspension comprising a population of adult cardiac stem cells;
(b) selecting cells that express at least SOX17 and GATA 4;
(c) expanding the cells that are selected in step (b); and
(d) confirming that the substantially pure population of stem cells that results from the expansion step (c) still express at least SOX17 and GATA 4. Preferably, confirming that the substantially pure population of stem cells that results from the expansion (c) expresses at least SOX17, GATA4 and IL-1β and does not express the following markers: Oct4, Nanog, C-kit, telomerase reverse transcriptase, CXCR4 protein and Nkx 2.5; and optionally confirming that the cells are able to differentiate into one or more of the following cells types: adipocytes, osteocytes, endothelial cells and smooth muscle cells.

The methods of the present invention may start from any known suspension comprising a population of adult cardiac stem cells. However, in a specific embodiment, the methods also include the preparation of the initial cell suspension comprising a population of adult cardiac stem cells. In one embodiment, this cell suspension is prepared from cardiac tissue such as a heart biopsy (e.g. obtained during cardiac surgery, by means of a biopsy catheter during cardiac catheterism, or from the hearts of sacrificed animals). Thus, in this embodiment, the method of the present invention comprises the steps of isolating a population of adult cardiac stem cells from cardiac tissue and expanding said population of cells before the step of selecting the cells. In this embodiment, the method of the invention comprises the steps of:

(a) preparing a suspension comprising cells from cardiac tissue;
(b) isolating a population of adult cardiac stem cells;
(c) expanding said population of adult cardiac stem cells; and
(d) selecting cells that express at least SOX17 and GATA4.

Preferably, step (d) comprises selecting cells that express at least SOX17, GATA4, IL-1β, and optionally CD31, and which do not express the following markers: Oct4, Nanog, c-kit, Telomerase reverse transcriptase, CXCR4 and Nkx 2.5; and that are able to differentiate into one or more of the following cells types: adipocytes, osteocytes, endothelial cells and smooth muscle cells.

Isolating a population of adult cardiac stem cells from cardiac tissue can be carried out by any means known in the art. In a specific embodiment, cells from cardiac tissue are filtered to remove cardiomyocytes and are immunodepleted for CD45-positive cells. The depleted cells may then optionally be immunoselected for CD117 (c-kit)-positive cells. However, the substantially pure population of adult cardiac stem cells according to the present invention is c-kit negative, so the inventors believe that this step is optional and may also not result in true immunoselection if present. It is possible that this step merely represents an additional size filtration step and could be replaced by filtration with beads that contain any immunoselective antibody or no antibody at all. Alternatively, the cells initially isolated using immunoselection for CD117 may result in an initial population of adult cardiac stem cells that express c-kit. However, it is clear that the substantially pure adult cardiac stem cell population of the invention is c-kit negative, meaning that any c-kit expression that may initially be present is lost in the subsequent selection step or selection and expansion steps. The marker profile of the cells may change between steps of the method, and in particular between the initial suspension comprising a population of adult cardiac stem cells and the cells that result from the selection step.

The step of expanding said population of adult cardiac stem cells may comprises growing the isolated population of adult cardiac stem cells in expansion medium under suitable conditions that are conducive to cell growth (e.g. at 3% O$_2$ atmosphere). The expanded population of adult cardiac stem cells may then be cryopreserved to create a working cell bank (WCB). For example, the population of adult cardiac stem cells may be cryopreserved at passage 4 after 21 duplications in order to make a WCB. The expression profile of the cells may then be analysed.

In a further specific embodiment, a method of preparing the substantially pure population of adult cardiac stem cells according to the present invention comprises the steps of:

(a) preparing a suspension comprising cells from cardiac muscle tissue;
(b) isolating a population of adult cardiac stem cells;
(c) expanding said population of adult cardiac stem cells;
(d) preparing a working cell bank (WCB) comprising a plurality of cell lines or working cell banks each having a cell line;
(e) selecting those cell lines from the working cell bank or from the working cell banks that express at least SOX17 and GATA 4; preferably selecting those cell lines from the working cell bank or from the working cell banks that express at least SOX17, GATA4, IL-1β, and optionally CD31, and do not express the following markers: Oct4, Nanog, c-kit, telomerase reverse transcriptase, CXCR4 protein and Nkx 2.5; and optionally confirming that the cells are able to differentiate into one or more of the following cells types: adipocytes, osteocytes, endothelial cells and smooth muscle cells.
(f) expanding the selected cell lines; and
(g) confirming the expression of at least SOX17 and GATA4 in the final, substantially pure population of adult cardiac stem cells, preferably confirming the expression in the final substantially pure population of adult cardiac stem cells of at least SOX17, GATA4, IL-1β, and optionally CD31, and the absence of expression of the following markers: Oct4, Nanog, c-kit, telomerase reverse transcriptase, CXCR4 protein and Nkx 2.5.

In a specific embodiment of this method of the invention, there is a further selection step between steps (b) and (c), comprising selecting cells that express at least SOX17 and GATA 4 for further processing. More specifically, an additional selection step is carried out after cells have been expanded at least for 3 passages, which may comprise 17 duplications. At passage 3, a cell pellet is obtained and cells expressing high levels of mRNA for SOX17 and GATA4 are selected and further expanded to form the Working Cell Bank. The cell phenotype is confirmed at the WCB stage by flow cytometry and qPCR, and cells expanded to give rise to the final product.

In any of the methods of the present invention, the selecting step and/or the confirming step may optionally also include selection for or detection of one or more further marker(s). These markers include WT1, HEY2, KDR, PDGF, CCL2, IL1α and/or CSF3. In one specific embodiment, the selection step(s) involves selecting for cells that express all of the markers SOX17, GATA4, WT1, and HEY2. In a further specific embodiment, the selection step involves selecting for cells that express all of the markers SOX17, GATA4, WT1, HEY2, KDR, PDGF-β, CCL2, IL1α and CSF3. In a specific embodiment, the confirming step involves confirming that the cells express all of the markers SOX17, GATA4, WT1, and HEY2.

The term "working cell bank" is used herein in the conventional sense and would be well understood to a person skilled in the art. A "working cell bank" is a culture of cells derived from a master cell bank or from primary populations of isolated cells and is intended for use in the preparation of production cell cultures that may be used to produce the pharmaceutical compositions of the invention (also referred to as the "final product").

Although it may be possible to generate the cells of the present invention by other methods, the present inventors have found that the step of selecting for cells that express at least SOX17 and GATA 4 increases the efficiency of production of substantially pure populations of adult cardiac stem cells that possess all of the advantageous properties of the claimed stem cell populations.

Cells and/or cell lines that have been selected from the WCB may then be thawed and expanded. In some embodiments, the selected cells lines may be expanded until passage 5 (25 duplications accumulated), thus making the Final Product (FP) in which cell quality was analysed. Quality Controls (QC) may be performed during the manufacturing process to ensure the identity, purity and safety of the final product.

The final verification step, to confirm the expression of at least SOX17 and GATA 4 in the final, substantially pure population of adult cardiac stem cells is useful for quality control purposes and to ensure that the final product is a substantially pure population of adult cardiac stem cells according to the invention.

The present invention also extends to adult cardiac stem cells and a substantially pure population of adult cardiac stem cells obtained or obtainable by the methods described herein.

The population of adult cardiac stem cells may be isolated in any suitable medium known in the art. The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase to which cells growing on a petri dish or other solid or semisolid support are exposed. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins. A basal medium generally serves as the basis for a more complex medium, to which supplements such as serum, buffers, growth factors, lipids, and the like are added. In one aspect, the growth medium may be a complex medium with the necessary growth factors to support the growth and expansion of the cells of the invention while maintaining their self-renewal capability. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-12, RPMI 1640, and Iscove's Modified Dulbecco's Medium (IMDM).

In a preferred embodiment, the isolation medium comprises EGF, bFGF, IGFII and ITS. The isolation medium may further comprise DMEM/F-12 medium, FBS, L-Glutamine, Penicillin-Streptomycin and/or hEPO. In a specific preferred embodiment, the isolation medium comprises one or more of the following components at the specified concentrations:
  DMEM/F-12 medium at a concentration of about 80-95%, for example 85-90%, or 86%, 87%, 88% or 89%;
  FBS at a concentration of about 5-15%, for example 7-13%, 8%-12% or 9%, 10%, 11% or 12%;
  Penicillin-streptomycin at a concentration of about 0.5-2%, for example 0.75%-1.5%, 0.8%-1.2%, or 0.9%, 1%, or 1.1%, or alternatively at a concentration of 100 U/ml and 100 µg/ml respectively;
  bFGF at a concentration of about 5-15 ng/ml, 7-13 ng/ml, 8%-12 ng/ml or 9 ng/ml, 10 ng/ml, 11 ng/ml or 12 ng/ml;
  EGF at a concentration of about 10-30 mg/ml
  IGF II at a concentration of about 20-40 ng/ml
  ITS at a concentration of about 0.01-1×, for example 0.25-0.75× or 0.5×; and/or
  hEPO at a concentration of about 0.0001-0.05 U/ml, for example, 0.001-0.01 U/ml, 0.0025-0.0075 U/ml or 0.004-0.006 U/ml, or 0.005 U/ml.

In a specific embodiment, the isolation medium comprises all of DMEM/F-12 medium, FBS, L-Glutamine, Penicillin-Streptomycin, EGF, bFGF, IGFII, ITS and hEPO.

The population of adult cardiac stem cells may be expanded in any suitable medium known in the art. In a preferred embodiment, the expansion medium comprises EGF, bFGF, IGFII and ITS. The expansion medium may further comprise DMEM/F-12 medium, Neurobasal medium, FBS-ESCq, L-Glutamine, Penicillin-Streptomycin, B27, N2, and/or β-mercaptoethanol.

In a specific preferred embodiment, the isolation medium comprises one or more of the following components at the specified concentrations:
  DMEM/F-12 medium at a concentration of about 40-50%, for example 42-45%, or 42%, 43%, 44% or 45%;
  Neurobasal medium at a concentration of about 40-50%, for example 42-45%, or 42%, 43%, 44% or 45%;
  FBS-ESCq at a concentration of about 5-15%, for example 7-13%, 8%-12% or 9%, 10%, 11% or 12%;
  L-Glutamine at a concentration of about 0.5 mM to 5 mM, for example 1 mM-3 mM, 1.5 mM-2.5 mM or 2 mM;
  Penicillin-streptomycin at a concentration of about 0.5-2%, for example 0.75%-1.5%, 0.8%-1.2%, or 0.9%, 1%, or 1.1%, or alternatively at a concentration of 100 U/ml and 100 µg/ml respectively;
  β-mercaptoethanol at a concentration of 40-60 µM, for example 45-55 µM, 47-52 µM or 50 µM;
  B27 at a concentration of 0.01-1×, for example 0.25-0.75× or 0.5×;
  N2 at a concentration of 0.01-1×, for example 0.25-0.75× or 0.5×;
  bFGF at a concentration of about 5-15 ng/ml, 7-13 ng/ml, 8%-12 ng/ml or 9 ng/ml, 10 ng/ml, 11 ng/ml or 12 ng/ml;
  EGF at a concentration of about 10-30 mg/ml;
  IGF II at a concentration of about 20-40 ng/ml; and/or
  ITS at a concentration of about 0.01-1×, for example 0.25-0.75× or 0.5×.

In a specific embodiment, the expansion medium comprises all of DMEM/F-12 medium, Neurobasal medium FBS ESCq, L-Glutamine, Penicillin-Streptomycin, B27, N2, β-mercaptoethanol, EGF, bFGF, IGFII and ITS.

Use of the media defined above for isolation and explosion of cardiac stem cells may lead to a few cells that possess the properties of the adult cardiac stem cells of the present invention. However, as identified in Lauden et al., (Circulation Research (2012) DOI: 10.1161/CIRCRESAHA.112.276501), without the selection step as described herein the cardiac stem cells may be Oct4 and Nanog positive, unlike the cells of the present invention. Thus, the selection step described herein is useful for producing a large population of adult cardiac stem cells according to the invention.

The methods of the present invention may be carried out under any suitable conditions that are conducive to cell growth. Exemplary culture conditions include a temperature of about 30-40° C., preferably about 35-38° C., 36-37.5° C. or about 37° C. The oxygen concentration may be from about 1-5%, for example from about 2-4% or 2.5-3.5%, or about 3%.

Methods of Treatment, Therapeutic Uses and Pharmaceutically Acceptable Compositions The adult cardiac stem cells of the invention, including cells obtained or obtainable by any of the methods described herein, are suitable for use in therapy and methods of treating ischemic injury and cardiovascular disease, particularly cellular therapies, including the induction of tissue repair/regeneration in vivo. The adult cardiac stem cells of the invention will generally be used in methods of treatment and therapeutic uses in the form of a substantially pure population of adult cardiac stem cells of the invention or in a mixed population of cells of the invention.

The invention therefore provides methods of treatment comprising administering the adult cardiac stem cells of the invention or the substantially pure population of adult cardiac stem cells of the invention or the mixed population of cells of the invention to a recipient subject, and also provides the adult cardiac stem cells of the invention or the substantially pure population of adult cardiac stem cells or the mixed population of cells of the invention for use in therapy.

In particular, adult cardiac stem cells of the invention or the substantially pure population of adult cardiac stem cells or the mixed population of cells of the invention are useful for treating ischemic injury and cardiovascular diseases such as myocardial infarction, chronic ischemic cardiomyopathy, cardiomyopathy and chronic heart failure. Due to the immunoregulatory capabilities of the cells of the invention they can be used for the treatment of autoimmune diseases, inflammatory process, chronic ulcers and wound healing in general. In addition they can be used to prevent allogeneic transplant organs rejection. As cells of the invention have angiogenic capabilities they can be used for ischemic affectations like critical limb ischemia.

The invention therefore provides methods of treating autoimmune diseases, inflammatory process, chronic ulcers and for promoting wound healing comprising administering the adult cardiac stem cells of the invention, the substantially pure population of adult cardiac stem cells of the invention, the mixed population of the invention or a pharmaceutical composition of the invention to a recipient subject. The invention also provides methods for preventing allogeneic organ transplant rejection comprising administering the adult cardiac stem cells of the invention, the substantially pure population of adult cardiac stem cells of the invention or the mixed population of cells of the invention to a recipient subject.

Generally the adult cardiac stem cells of the invention or the substantially pure population of adult cardiac stem cells of the invention or the mixed population of cells of the invention is introduced into the body of the subject by injection or implantation. Generally the adult cardiac stem cells of the invention or the substantially pure population of adult cardiac stem cells of the invention or the mixed population of cells of the invention will be directly injected into the tissue in which they are intended to act. In specific embodiments, the adult cardiac stem cells of the invention, the substantially pure population of adult cardiac stem cells of the invention, the mixed population of cells of the invention or a pharmaceutical composition of the invention is administered intravenously, intra-arterially, intracoronarily or intramyocardially.

The adult cardiac stem cells of the invention may be administered at a dose of $1 \times 10^6$ to $50 \times 10^6$ cells, preferably at a dose of $25 \times 10^6$ to $45 \times 10^6$ cells, more preferably at a dose of $35 \times 10^6$ to $40 \times 10^6$ cells, and most preferably at a dose of $38 \times 10^6$ cells.

In one embodiment, the adult cardiac stem cells of the invention or the substantially pure population of adult cardiac stem cells of the invention or the mixed population of cells of the invention may be used in the regeneration of cardiac tissue, including in the regeneration of myocardium. In this embodiment, the cells of the invention may be injected or implanted directly into the damaged cardiac tissue trans-endocardically; using a needle catheter which injects the cells into the myocardium, intra-arterially; using a balloon catheter into the artery irrigating the damaged tissue area, or retrograde; by injecting the cells into the coronary vein draining the damaged area. An alternative embodiment for the treatment of the myocardium is a transcatheter injection transendocardically, with or without electric mapping with a system such as the NOGA system or any similar injection system. In one embodiment, the invention provides adult cardiac stem cells of the invention, a substantially pure population of adult cardiac multipotent stem cells of the invention, or a mixed population of cells of the invention, optionally adhered to a biocompatible implant, for use in the regeneration of cardiac tissue.

In another embodiment, the substantially pure population of adult cardiac stem cells of the invention or the mixed population of cells of the invention may be implanted into the damaged tissue adhered to a biocompatible implant. Within this embodiment, the substantially pure population of adult cardiac stem cells of the invention or the mixed population of cells of the invention may be adhered to the biocompatible implant in vitro, prior to implantation into the subject. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the substantially pure population of adult cardiac stem cells of the invention or the mixed population of cells of the invention may be embedded in a matrix, prior to implantation of the matrix into the subject. Generally, the matrix will be implanted into the damaged tissue of the subject. Examples of matrices include collagen based matrices, fibrin based matrices, laminin based matrices, fibronectin based matrices and artificial matrices. This list is provided by way of illustration only, and is not intended to be limiting.

In a further embodiment, the substantially pure population of adult cardiac stem cells of the invention or the mixed population of cells of the invention may be implanted or injected into the subject together with a matrix forming component. This may allow the cells to form a matrix following injection or implantation, ensuring that the cells remain at the appropriate location within the subject. Examples of matrix forming components include fibrin glue liquid alkyl, cyanoacrylate monomers, plasticizers, polysaccharides such as dextran, ethylene oxide-containing oligomers, block co-polymers such as poloxamer and Pluronics, non-ionic surfactants such as Tween and Triton '8', and artificial matrix forming components. This list is provided by way of illustration only, and is not intended to be limiting. It will be clear to a person skilled in the art, that any combination of one or more matrix forming components may be used.

In a further embodiment, the substantially pure population of adult cardiac stem cells of the invention or the mixed population of cells of the invention may be contained within a microsphere. Within this embodiment, the cells may be encapsulated within the centre of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

For use in therapy and methods of treatment, the substantially pure population of adult cardiac stem cells or the mixed population of cells of the invention will be delivered to the subject in a therapeutically effective amount. The number of cells to be delivered in vivo or ex vivo is based on a number of parameters, including: the body weight of the subject, the severity of tissue damage, and the number of cells surviving within the subject. A typical number of cells may be around $1 \times 10^6$ to $1 \times 10^8$ cells, more particularly $10^5$ to $10^7$ cells per kg body weight. Generally, the total number of cells delivered to the subject in a single treatment regimen will be about $1 \times 10^6$ to $50 \times 10^6$ cells.

As mentioned above, the substantially pure population of adult cardiac stem cells of the invention possesses several characteristics that make them particularly well suited for use in therapeutic applications. In particular, the low immunogenicity, the ability to modulate the T cell response in the recipient, the ability to induce angiogenesis and the ability to promote cardio-regeneration and induce regeneration of endogenous cardiomyocytes may all contribute to therapeutic efficacy. The invention therefore provides a method of treating cardiovascular disease and/or the therapeutic use of the substantially pure population of adult cardiac stem cells of the invention for the treatment of cardiovascular disease, wherein the substantially pure population of adult cardiac stem cells induce cardiac tissue repair by one or more of the following mechanisms:

(a) recruitment of monocytes;
(b) immunomodulation;
(c) activation of angiogenesis;
(d) promote cardio-regeneration and/or
(e) inducing regeneration of endogenous cardiomyocytes.

Thus, in one embodiment the invention provides a method of treating a subject suffering from a cardiovascular disease or ischemic injury comprising the step of administering to the subject the adult cardiac stem cells of the invention, a substantially pure population of adult cardiac multipotent stem cells of the invention, a mixed population of the invention or a pharmaceutical composition of the invention. The low immunogenicity of the substantially pure population of adult cardiac stem cells of the invention and/or the immunomodulatory ability of the substantially pure population of adult cardiac stem cells of the invention allows the substantially pure population of adult cardiac stem cells of the invention to avoid acute rejection and/or elimination by the recipient subject's immune system after administration. Thus, for a period of at least 24 hours, e.g. 36 hours, 48 hours, 72 hours, 4 days, 5 days, 6 day, 1 week, 2 weeks, one month or more, a detectable amount of the administered cells are still present in the subject. In a specific embodiment, after 24 hours, at least about 50% or more, for example at least about 60%, 70%, 80%, 90%, 95%, 99% or more, of the administered cells are still present in the subject.

This retention of the administered cells allows the cells to carry out their function in treating the cardiovascular or ischemic disease. For example, the cells are able to exert their immunomodulatory effect, induce monocyte recruitment and/or activation, induce angiogenesis and/or induce regeneration of endogenous cardiomyocytes for a period of time up to about 24 hours or more, for example up to 36 hours, 48 hours, 72 hours, 4 days, 5 days, 6 day, 1 week, 2 weeks, one month or more.

Although cells from the administered substantially pure population of adult cardiac stem cells of the invention may remain in the subject for a time sufficient to exert a therapeutic effect, the cells are not retained permanently in the subject. The time sufficient to exert a therapeutic effect is at least 24 hours and may be up to one month or more. For example, the cells may be retained for up to 36, 48, 72 hours, 4 days, 5 days, 6 day, 1 week, 2 weeks, or one month.

A further beneficial property of the adult cardiac stem cells and the substantially pure population of adult cardiac stem cells of the invention is that they do not induce tumours in immunodeficient subjects after administration, as described in Example 4E.

The adult cardiac stem cells and the substantially pure population of adult cardiac stem cells of the invention can also be administered at a dose of at least $50 \times 10^6$ cells by intracoronary administration without any evidence of cardiac toxicity. In the context of the invention, cardiac toxicity is measured by detecting the presence or absence of elevated levels of certain cardiac enzymes above the accepted normal limits. In particular, the level of cardio Troponin I (cTnI), Creatine Kinase-MB (CK_MB) and/or Myoglobin (Mb) are indicative of cardiac toxicity. As described herein in Example 4D, the level of these enzymes is not elevated following administration of the substantially pure population of adult cardiac stem cells of the invention to a subject. The invention also provides a pharmaceutical composition comprising: (a) the adult cardiac stem cells of the invention, (b) a substantially pure population of adult cardiac stem cells of the invention, or (c) a mixed population of cells of the invention, and a pharmaceutically acceptable carrier. Preferably, the pharmaceutical composition of the invention comprises from $1 \times 10^6$ to $50 \times 10^6$ cells, preferably $25 \times 10^6$ to $45 \times 10^6$ cells, more preferably $35 \times 10^6$ to $40 \times 10^6$ cells, most preferably $38 \times 10^6$ cells.

The pharmaceutically acceptable carrier may comprise a cell culture medium which supports the cells' viability. The medium will generally be serum-free in order to avoid provoking an immune response in the recipient. The carrier will generally be buffered and/or pyrogen-free.

Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. In many embodiments, the solution is stable under the conditions of manufacture and storage and preserved against the contaminating action of microorganisms such as bacteria and fungi through the use of, for example, parabens, chlorobutanol, phenol, ascorbic acid, thimerosal. This list is provided by way of illustration only, and is not intended to be limiting. Solutions that are adult stem cell compositions of the invention can be prepared by incorporating adult stem cells as described herein in a pharmaceutically acceptable carrier or diluent and, as required, other ingredients enumerated above, which has been sterilized by filtration.

Some examples of materials and solutions which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. This list is provided by way of illustration only, and is not intended to be limiting.

In a specific embodiment, the substantially pure population of adult cardiac stem cells of the invention or the pharmaceutical composition of the invention may be frozen in freezing medium. Any medium that preserves the viability of the cells at temperatures below about −20° C. (e.g. temperatures below about −40° C., or about −80° C.) is suitable as freezing medium. For example, the freezing medium may comprise 2.5% to 10% DMSO. More specifically, the freezing medium may comprise 5-7.5% DMSO.

Freezing medium may be based on culture medium or expansion medium described herein, further comprising foetal bovine serum or human serum or any other protein or mix of proteins able to maintain cell integrity after thawing the cells. Cells of the invention can also be frozen in protein free mediums based on dextrans.

After thawing, cells of invention can be washed to remove the DMSO or other freezing medium components before administration or re-suspension in administration solution. Administration solution will be any physiological solution able to be injected in patients without toxicity. Administration solution may comprise 3-15% protein such as human serum albumin.

The pharmaceutical compositions of the invention may also be used in any of the methods of treatment or therapeutic uses described herein.

General Definitions

The term "about" in reference to a numeric value means+/−10% of that numeric value. The term "about" in reference to a numeric value also includes +/−5% of that numeric value The terms "comprise" and "comprising" are used in the inclusive, open sense, meaning that additional elements may be included. The term comprises also encompasses and may be used interchangeably with the terms "consists of" and "consists essentially of"

The term "substantially pure" includes "completely pure" and may be used interchangeably with that term.

E) and F) CSCs are able to form cardiospheres and to growth in suspension when a single cell is seeded in an ultra-low adherent plate.

Figure 9:
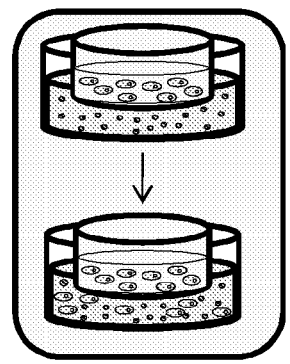
Figure 9:
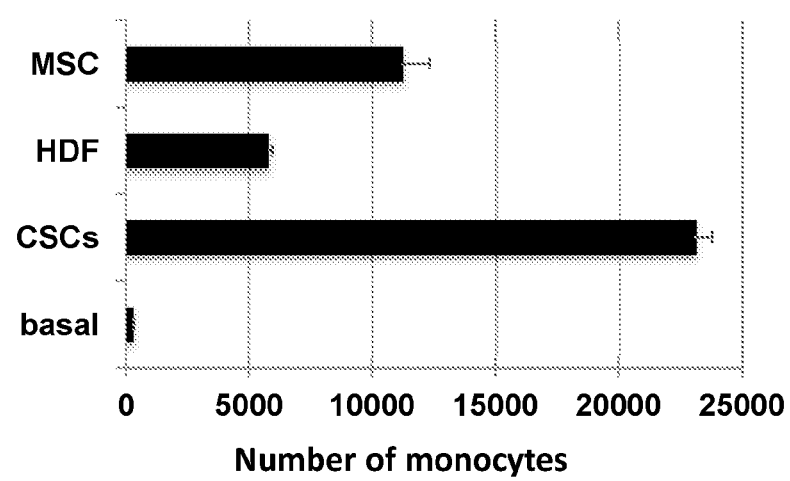
Figure 9:
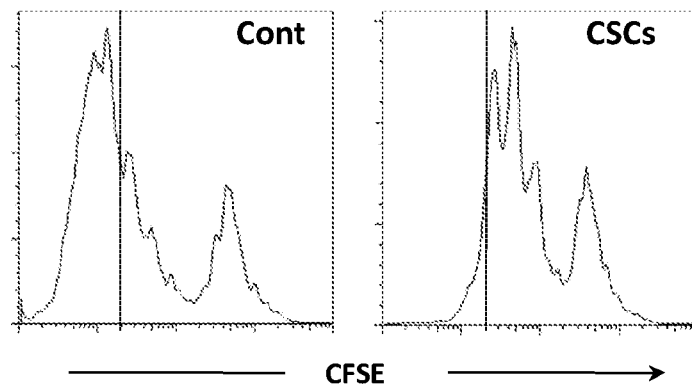

FIG. 9. A) Cell migration assay trans-well plate.

B) CSCs have a strong recruitment capability over monocytes.

C) CSCs demonstrated immunoregulatory capacity on activated T lymphocytes.

Figure 10:
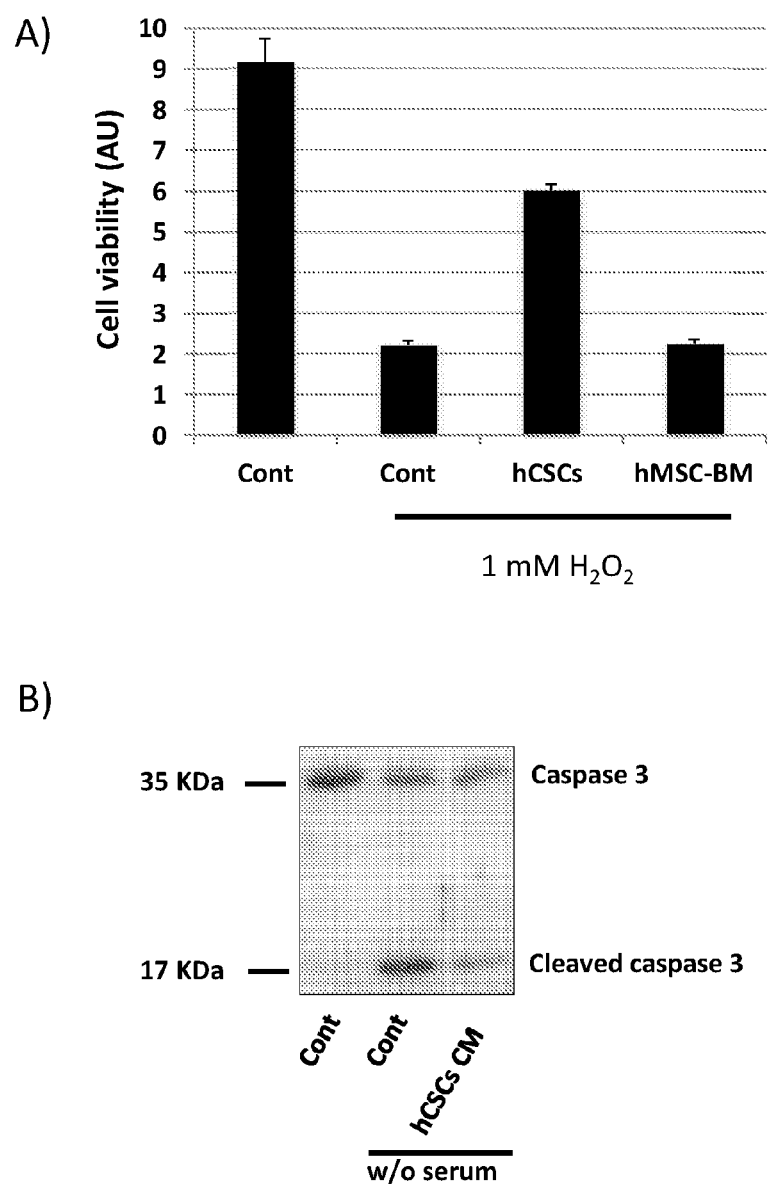

FIG. 10. A) Growth factors secreted by the CSC promote survival.

B) The pro-survival ability of the factors secreted by the CSCs was also assayed in H9c2 cells after serum deprivation.

Figure 11:
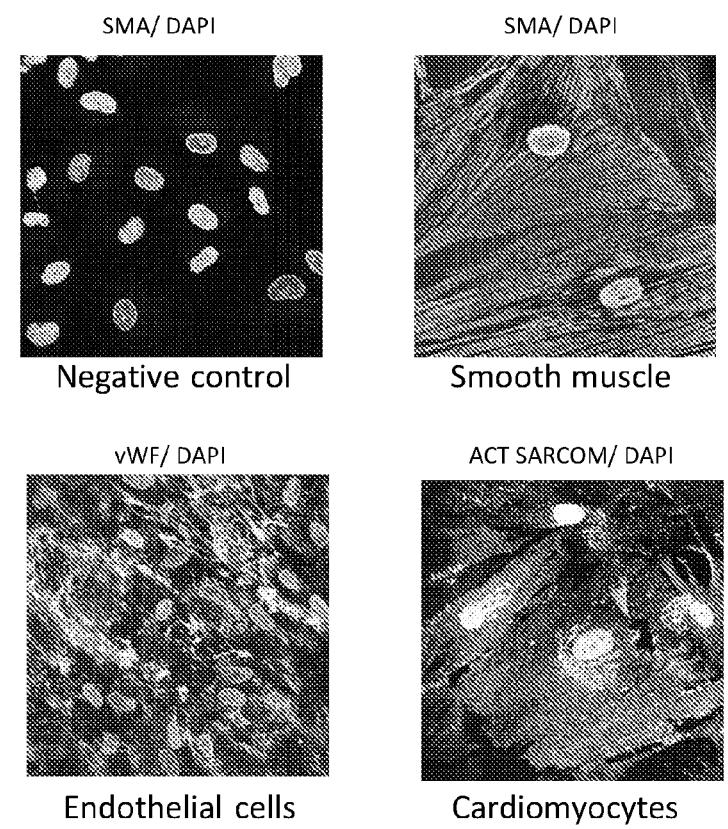
Figure 11:
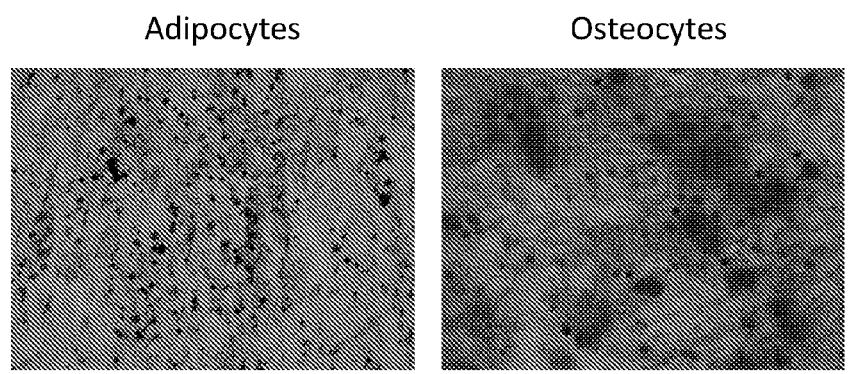

FIG. 11. A) Differentiation potential of CSCs to cardiac lineages is analyzed by immunofluorescence. CSC cells demonstrated expression of markers corresponding to smooth muscle, endothelial cells and cardiomyocytes after culture in specific differentiation medium.

B) In addition, CSCs were also able to differentiate to adipocytes and osteocytes after culturing in the appropriated medium. Adipocytic differentiation was analyzed by oil red O staining (to show cytoplasmic lipidic droplets) and osteocytic differentiation confirmed by Alizarin red staining (to indicate calcium deposits).

Figure 12:
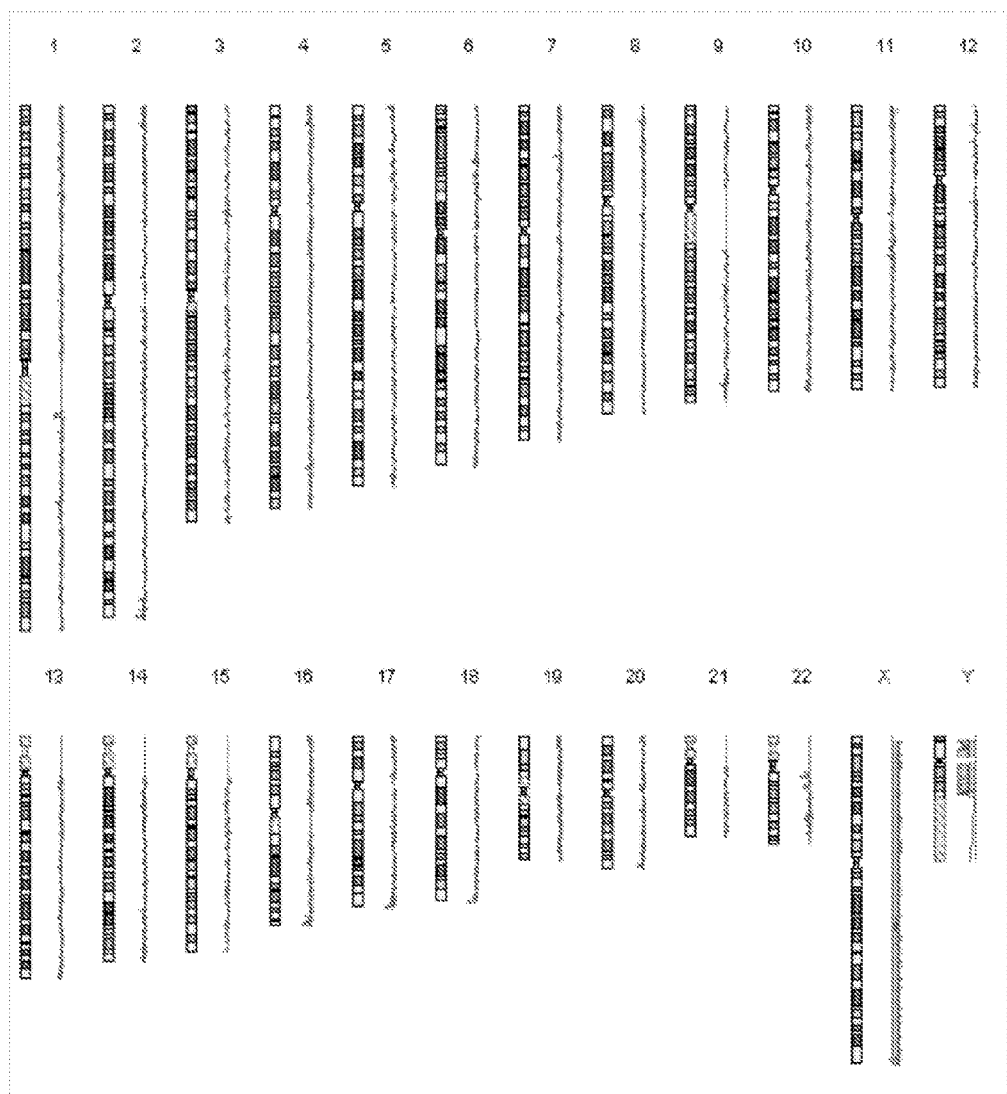

FIG. 12. The comparative Genome Hybridization analysis shown in the figure correspond to a human female genome and not chromosomal alterations such as duplications or deletions, are observed.

Figure 13:
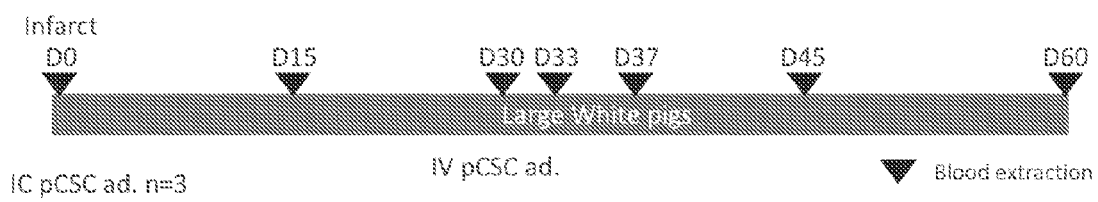
Figure 13:
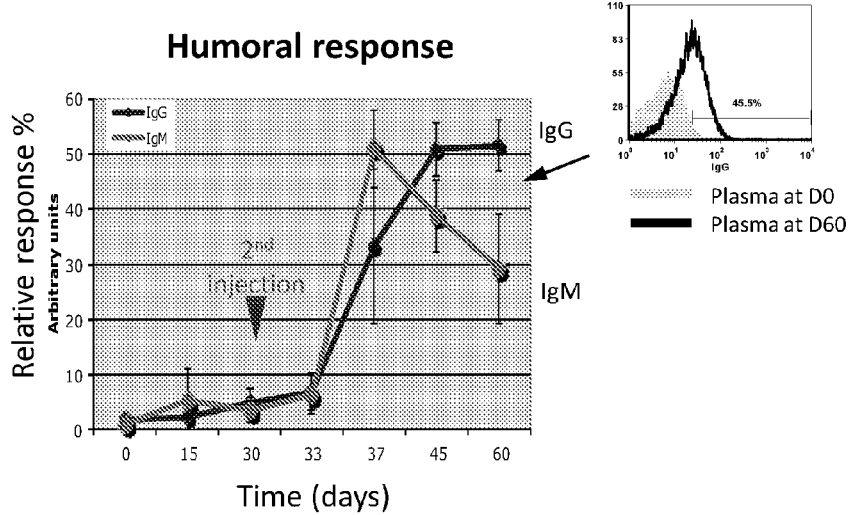

FIG. 13. Allogeneic CSCs do not induce a strong humoral response after intracoronary administration.

A) Allogeneic pig CSCs were intracoronary injected in immunocompetent infarcted pigs and blood samples collected before cell administration or after 15 or 30 days. At day 30 a new dose of the same cells was intravenous injected and blood samples collected at days 3, 7, 15 and 30 after the second injection.

B) The presence of specific immunoreactive immunoglobulins (IgG and IgM) was analyzed in the different blood samples. It was not possible to find specific immunoreactive IgG against the injected cells during the first 30 days. On the contrary, after the second injection we observed the presence of allogeneic CSCs specific IgM and IgG at days 7, 15 and 30. These results indicate that although allogeneic CSCs do not trigger a strong humoral response after administration they are recognized and probably eliminated by the immune system generating an immunological memory that induce a stronger and faster response after a second administration.

Figure 14:
Figure 14:
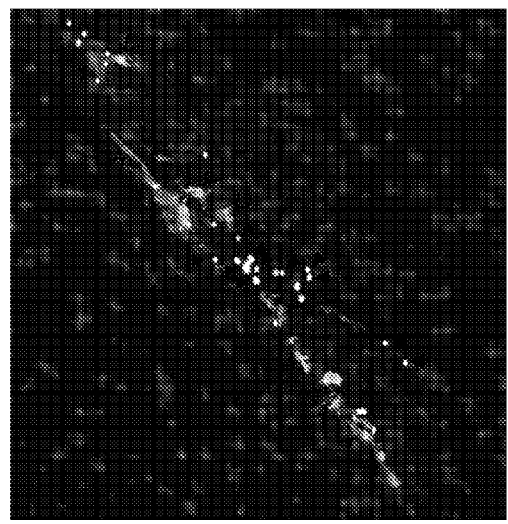

FIG. 14. CSCs stay in the heart at least 24 h after administration. Tracing experiments using GFP labeled cells demonstrated that CSCs remains in the infarcted area at least 24 h following injection. Human CSC were labeled with GFP (>) and injected into the myocardium of immunodeficient rats 7 days after they were infarcted. 24 h later animals were sacrificed and the presence of GFP positive cells analyzed by histology. Fluorescent-labeled microspheres were co-injected with the cells to be able to identify the administration place (filled arrowheads). Cell nuclei were stained with DAPI (*).

Figure 15:
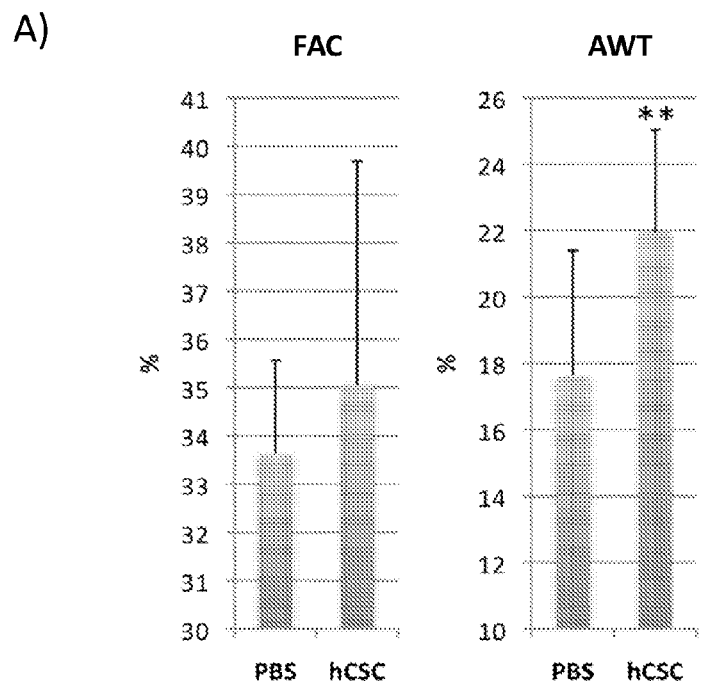
Figure 15:
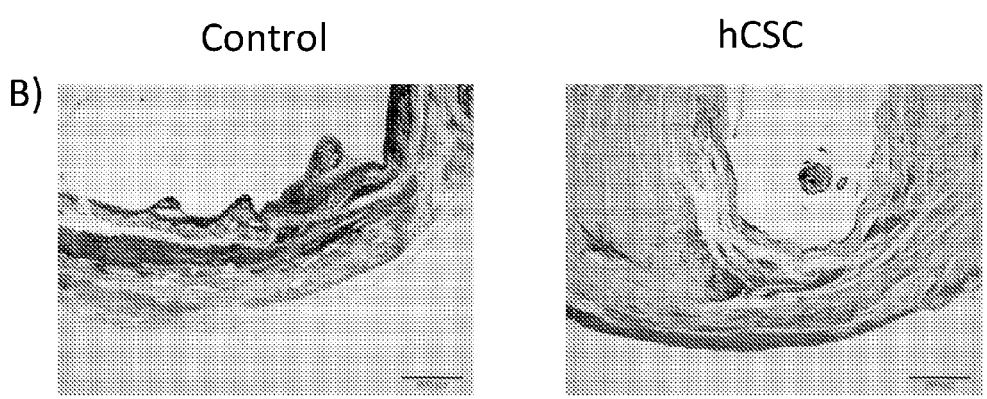

FIG. 15. A) Immunodeficient rats were infarcted by ligation of the anterior coronary descendent artery and CSCs from different donors intramyocardial transplanted ($5 \times 10^5$) and compared with animals injected with PBS. The Anterior Wall (AW) thickening was significantly higher in animals transplanted with CSCs.

B) Histological analysis using Masson's tricromic stain also showed a significant reduction of the scar size and an increase in cardiomyocytes in the affected area, in rats treated with cells when compared to control animals.

Figure 16:
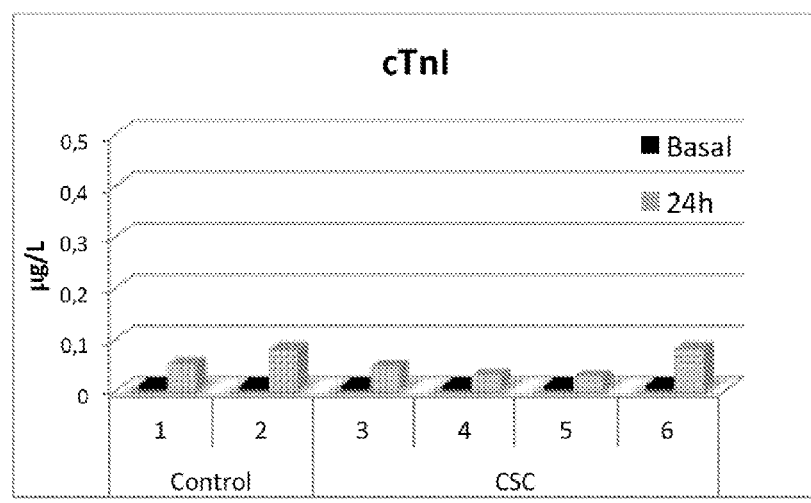

FIG. 16. Administration solution (placebo) or doses of $50 \times 10^6$ human CSC have been intracoronary injected in healthy pigs. Cardiac enzymes were tested at basal and 24 h after cell administration and no toxicity was observed.

Figure 17:
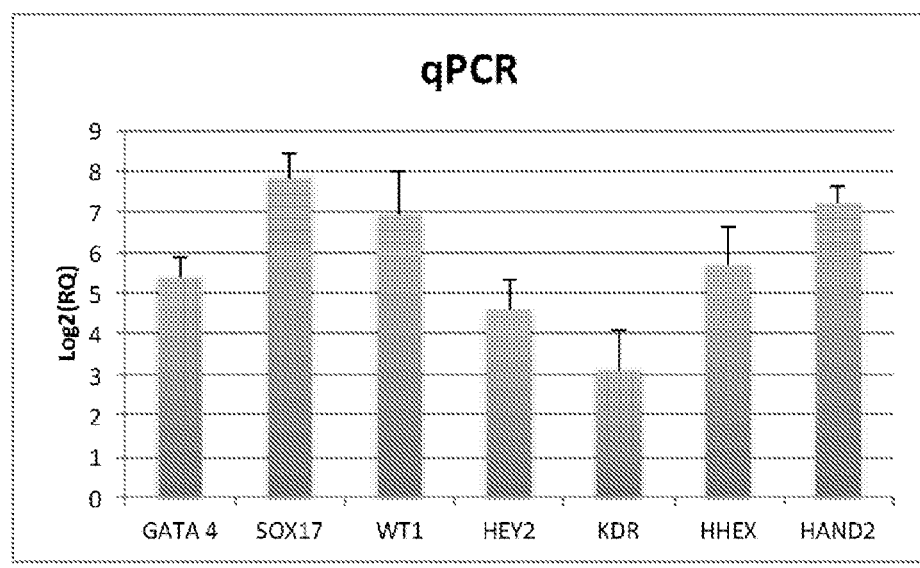

FIG. 17. Quantitative PCR (qPCR) analysis using specific probes (TaqMan probes from Life Technologies) showed that GATA4, SOX17, WT1, HEY2, KDR, HHEX and HAND2 are over-expressed in CSCs when compared with MSCs used as reference cell line. The gene GUSB was used as an endogenous control gene. The values are the Log 2 of the Relative Quantitation.

Figure 18:
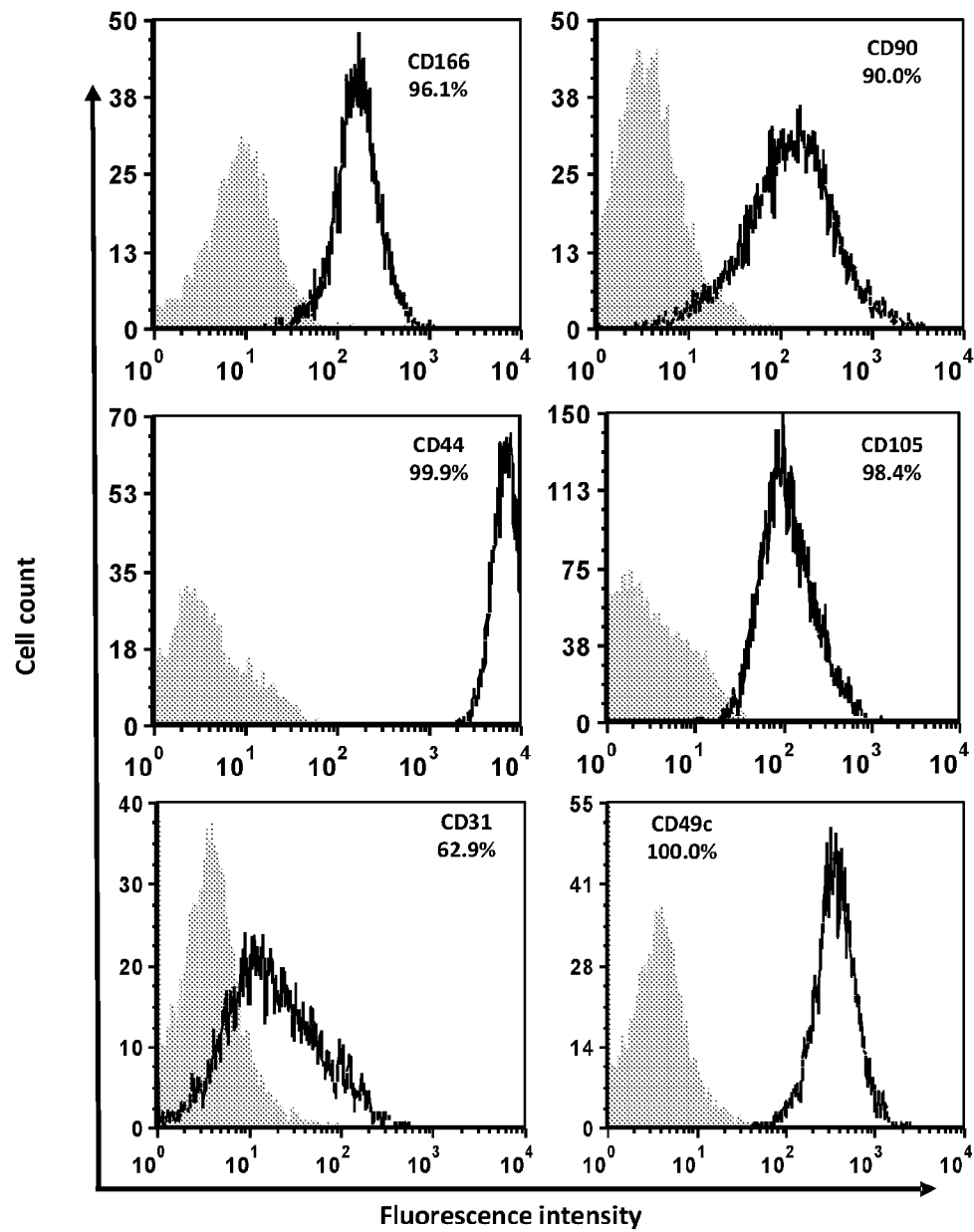

FIG. 18. Flow cytometry analysis reveals that CSCs express high levels of CD166, CD90, CD44, CD105, CD31 and CD49c (black histograms) on their cell membranes. Isotype controls are shown in the grey filled histograms.

EXAMPLES

Example 1—Cell Isolation and Expansion

The cells of the invention were isolated from cardiac biopsies obtained from the right atrial appendage and from the hearts of sacrificed animals (mice, rats, pigs, etc.). A cellular suspension was obtained by mincing the biopsies into small pieces (<1 mm$^3$) and treating with collagenase type 2 (Worthington Biochemical Corporation, Lakewood, N.J., USA) for 3 cycles of 30 min each. Cardiomyocytes were removed by centrifugation and filtration using 40 μm cell strainers. Cardiac stem/progenitor cells were obtained after immunodepletion of CD45-positive cells and selection of CSCs using microbeads (Miltenyi Biotech, Bergish Gladbach, Germany), and following manufacturer recommendations. The microbeads that were used were CD117 (c-kit) microbeads, but other microbeads could also be used because the isolation of CSCs is not reliant on the presence of c-kit.

After isolation, the cells were seeded in Matrigel (BD Biosciences, Madrid, Spain)-coated plates in isolation medium (DMEM/F12 medium supplemented with 10% fetal bovine serum embryonic stem cell qualified (FBS ESCq), L-Glutamine (2 mM), Penicillin-Streptomycin (100 U/mL and 100 μg/mL), bFGF (10 ng/mL) and ITS (Invitrogen, Madrid, Spain and Saint-Aubin, France), IGF-II (30 ng/mL) and EGF (20 ng/mL) (Peprotech, Neuilly-sur-Seine, France) and hEPO (Sigma-Aldrich, Madrid, Spain) (see Table 1).

TABLE 1

| CSC isolation medium | | |
|---|---|---|
| CSC isolation | DMEM/F12 | 89% |
| | FBS-ESCq | 10% |
| | Penicillin/Stre | 1% |
| | bFGF | 10 ng/mL |
| | EGF | 20 ng/mL |
| | IGF II | 30 ng/mL |
| | ITS | 0.5 x |
| | hEPO | 0.005 U/mL |

The cells were grown at 37° C. in a 3% O$_2$ atmosphere, thereby facilitating proper functioning and mimicking physiologic/pathologic conditions. One week after cell seeding, isolation medium was replaced by expansion medium, which is a combination of DMEM/F12 and Neurobasal medium (1:1) supplemented with 10% FBS ESCq, L-Glutamine, Penicillin-Streptomycin, B27 (1×), N2 (1×), β-mercaptoethanol (50 μM), ITS and growth factors (bFGF, IGF-II, EGF) (see Table 2).

TABLE 2

| Expansion medium | | |
|---|---|---|
| Expansion medium | DMEM/F12 | 44% |
| | Neurobasal | 43% |
| | 2-mercaptoet | 50 μM |
| | L-Glutamine | 2 mM |
| | FBS-ESCq | 10% |
| | Penicillin/Stre | 1 x |
| | B27 | 0.5 x |
| | N2 | 0.5 x |
| | bFGF | 10 ng/mL |
| | EGF | 20 ng/mL |
| | IGF II | 30 ng/mL |
| | ITS | 0.5 x |

The cells were grown in expansion medium at 3% $O_2$ atmosphere and then cryopreserved at passage 4 after 21 duplications in order to make a Working Cell Bank (WCB). The expression profile of the cells was then analysed. Cells with the right expression profile were thawed and expanded until passage 5 (25, duplications accumulated), thus making the Final Product (FP) in which cell quality was analysed. Quality Controls (QC) are done during the manufacturing process to ensure the identity, purity and safety of the final product.

Example 2—Characterization of mRNA and Protein Expression in CSCs

A. CSCs Express SOX17 and GATA4 mRNAs

The mRNA expression of SOX17 and GATA4 in the cardiac stem cells (CSCs) obtained by the method of Example 1 was compared to mesochymal stem cells (MSCs) from bone marrow or from adipose tissue. mRNAs from CSCs and from MSCs were isolated and cDNA produced for the qPCR and expression arrays experiments.

Figure 1:
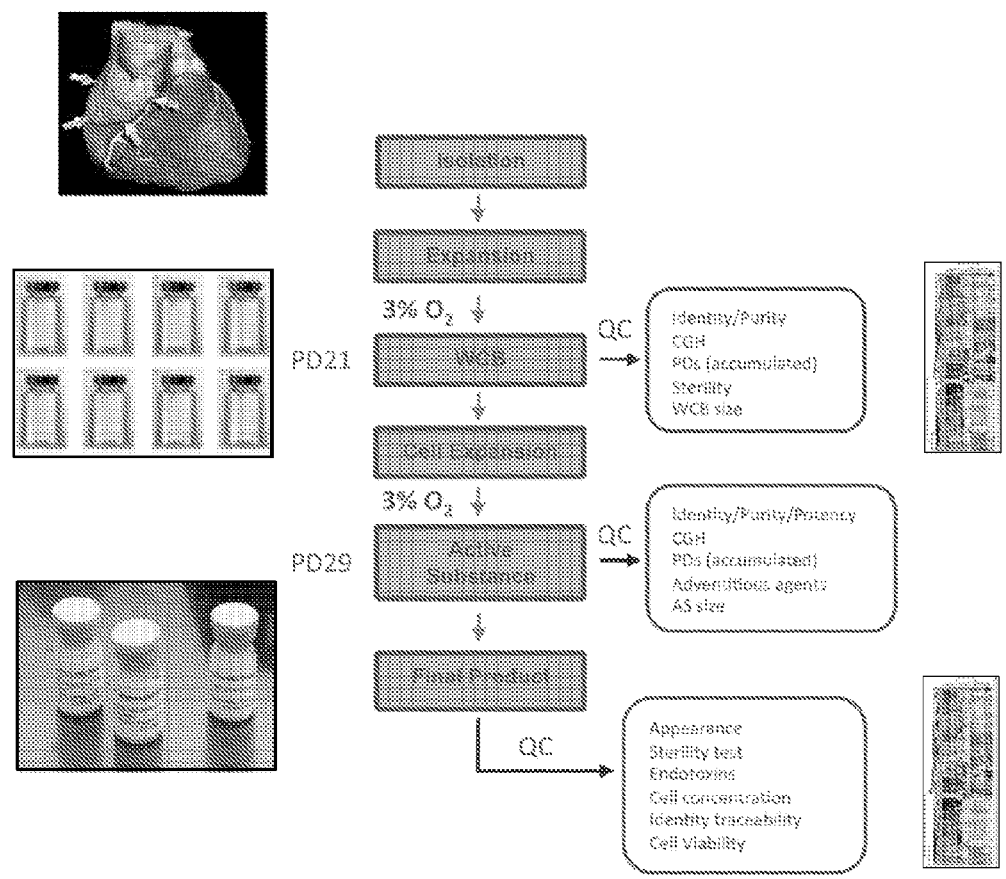
FIG. 1. Schematic representation of a protocol for production of the cardiac stem cells of the invention.
Figure 2:
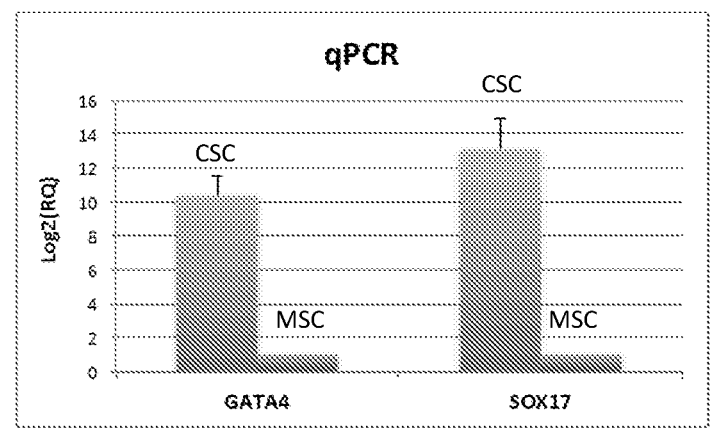
FIG. 2. A) Cardiac Stem Cells (CSCs) of the invention have a higher mRNA expression (as determined by qPCR) for SOX17 and GATA4 when compared to MSC from bone marrow or from adipose tissue.
B) CSCs express SOX17 and GATA4 proteins, as it can be observed in protein expression array studies.
Figure 2:
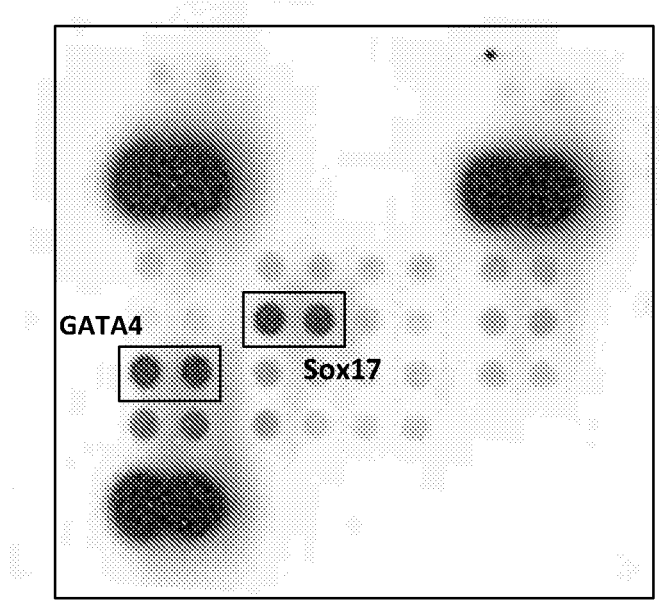

For the expression array experiments, RNA from $1\times10^6$ CSCs or MSCs from adipose tissue was isolated using Qiagen columns (RNeasy columns) and RNA quality analysed by a Bioanalyzer assay (Agilent Technologies). Only RNA preparations with a RIN>7 were amplified and labelled using the Low Input Labeling Kit (Agilent Technologies). The studies were done with 8 different donor of CSCs at WCB level and 6 at the FP level. As reference samples, 4 different donors of MSCs at WCB and 4 at FP were used. The microarray expression SurePrint G3v2, 60K platform was used and the analysis was done using GeneSpring v12.1 software. Statistical significance (p-values corrected) was calculated using One-Way Analysis of Variance (ANOVA) and corrected by multiple test (Benjamini-Hochberg). A p-value corrected <0.05 was considered statistically significant. As shown in FIG. 2A, the SOX17 and GATA4 mRNA expression was over 20-fold higher in CSCs than in MSCs from adipose tissue.

Confirmation of the microarray expression analysis was sought using qPCR. CSCs and human MSCs were harvested and total RNA isolated using TRI-Reagent (Sigma-Aldrich) according to the manufacturer's instructions. The RNA concentration was determined by photometric measurement. cDNA was synthesised from 2 μg RNA using the SuperScript® III First Strand Synthesis System for RT-PCR (Invitrogen) according to the manufacturer's instructions. The synthesized cDNA was diluted 1:10 and 50-200 ng of cDNA was subjected to quantitative real-time PCR (qPCR) using human-specific TaqMan probes (Applied Biosystems, see Table 3). qPCR reactions were performed in triplicates using TaqMan Universal PCR Master Mix (Applied Biosystems). PCR reactions were run on a StepOnePlus (Applied Biosystems) machine and StepOne Software v2.2.2 and Data Assist v3.0 software were used to analyze results. Expression of mRNAs was normalized to expression of beta Glucoronidase. For RQ calculation (2-AACT) human bone marrow MSCs were used as reference cell line.

TABLE 3

| list of primers for TaqMan qPCR analysis | |
|---|---|
| Target | Reference number |
| GATA4 | Hs00171403_m1 |
| SOX17 | Hs00751752_s1 |
| WT1 | Hs01103751_m1 |
| HEY2 | Hs00232622_m1 |
| KDR | Hs00911699_m1 |
| Telomerase | Hs00972656_m1 |
| GUSB | Hs99999908_m1 |
| HHEX | Hs00242160_m1 |
| HAND2 | Hs00232769_m1 |
| Nkx2.5 | Hs00231763_m1 |

The higher level of mRNA expression for SOX17 and GATA4 in CSCs relative to human MSC was confirmed using this method, as shown in FIG. 2B.

B. CSCs Express SOX17 and GATA4 Proteins

Protein expression array studies were performed to determine whether the GATA4 and SOX17 mRNAs are translated. Pellets of $10\times10^6$ cells were prepared from cultures in the linear phase of growth, washed twice with PBS and stored dry at −80° C. Before doing the hybridization, pellets were thawed and CSC lysates were prepared according to manufacturer's instructions. The protein concentration in each cell lysate was quantified.

The array studies were done using Proteome profilers human arrays kits, namely the proteome Profiler Human Cytokine Array Kit Panel A (ARY005) and a human pluripotent stem cell array kit (ARY010). The lysates (200 μg of protein extract) were mixed with antibodies against proteins present in the arrays (human cytokines and stem cell regulation proteins) and then the protein-antibodies complexes were incubated with the membrane. Hybridization with the antibody array membrane was performed according to the manufacturer's instructions. CSCs were found to express SOX17 and GATA4 proteins (FIG. 2B).

C. CSCs Express CD166, CD90, CD44 and CD105 but do Not Express c-kit, CD45, CD34 and CD11b The expression of c-kit, CD45, CD34, CD11b, CD166, CD90, CD44 and CD105 was determined by flow cytometry. Cells were released with trypsin-EDTA and resuspended in DMEM. Cell viability was found to be >85% by Trypan Blue dye exclusion technique. The cells were centrifuged and resuspended in PBS at a concentration of $0.2\text{-}1.0\times10^6$ cells/ml. Prior to staining, cells were blocked with 1% (v/v) human serum in PBS for 20 minutes on ice. About $0.5\text{-}3.0\times10^5$ cells were stained with saturating concentrations of surface marker specific antibodies and isotype matched controls. The cells were incubated in the dark for 1 hour at 4° C. After incubation, the cells were washed two times with PBS. When primary antibodies were in purified format, the cells were additionally incubated with fluorochrome-conjugated species-specific anti-Ig antibody for 20 minutes in the dark at 4° C. The number of cells staining positive for a given marker was determined by the percentage of cells present within a gate established such that fewer than 2% of the positive events measured represented non-specific binding by the isotype matched control. A minimum of 2,500 events was counted for each analysis. The expression of cell surface markers was analysed by flow cytometry using commercial antibodies at the dilutions recommended by the manufacturer. Cells were acquired using the Epics XL flow cytometer (Beckman Coulter) and analysed using FCS Express 3 software.

TABLE 4

Antibodies used in flow cytometric analysis

| Target | Clone | Source | LABEL |
|---|---|---|---|
| Anti-cKit | A3C6E2 | Milteyi | PE |
| Anti-cKit | 104D2 | BD | PE |
| CD45 | 2D1 | BD | FITC |
| CD11b | ICRF44 | SEROTEC | PE |
| CD34 | 581 | BD | PE |
| CD40 | 5C3 | BD | PE |
| CD80 | L307.4 | BD | PE |
| CD86 | IT2.2 | BD | PE |
| CD166 | 3A6 | BD | PE |
| CD90 | 5E10 | BD | FITC |
| CD44 | IM7 | EBIOSCIE | PE |
| CD105 | SN6 | THERMO SCIENTIFIC | FITC |
| HLA class I | W6/32 | SEROTEC | FITC |
| CD49c | C3II1 | BD | PE |
| CD133 | AC133 | Milteyi | PE |
| CXCR4 | 12G5 | BD | Non-labeled |
| CD31 | WM56 | BD | PE |

Figure 3:
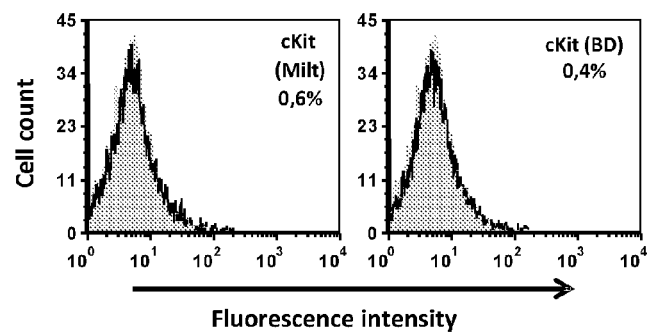
FIG. 3. A) No c-kit or very low expression is observed by flow cytometry analysis in CSCs. Representative expression of c-kit (black line) is shown. Grey filled area shows the isotype control.
B) Flow cytometry analysis reveals that CSCs are negative for the expression of CD45, CD11b, CD34, CXCR4 and CD133 on their cell membranes. The expression of CD45, CD11b, CD34, CXCR4 and CD133 (black histograms) against isotype controls (grey filled histograms) is shown.
Figure 3:
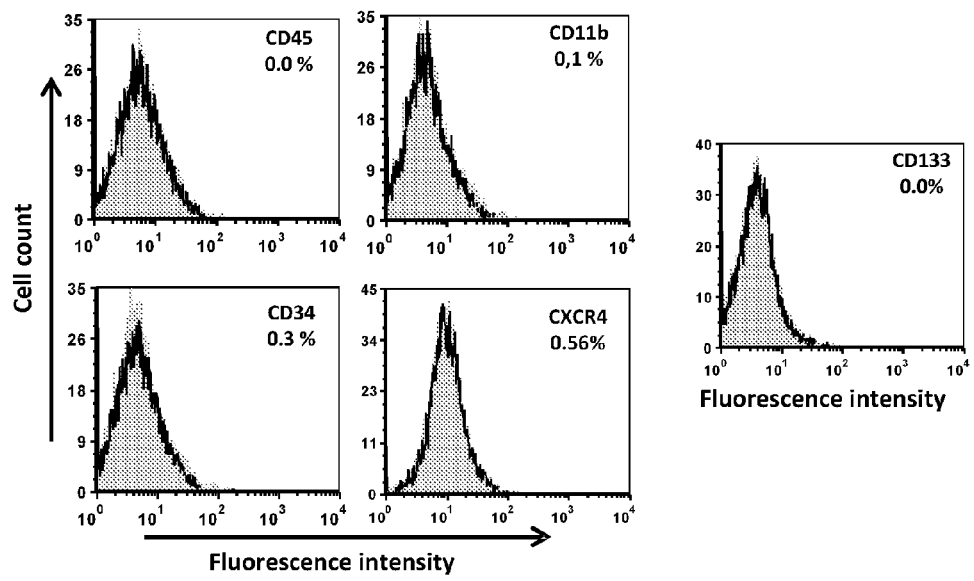

As shown in FIG. 3A, no c-kit or very low expression was observed in CSCs. Similar results were obtained using two different antibodies (one obtained from Miltenyi and the other from BD).

As shown in FIG. 3B, CSCs were also found to be negative for the lineages markers CD45, CD11b and CD34. As shown in FIG. 18, CSCs express CD166, CD90, CD44 and CD105.

D. CSCs do Not Express Telomerase

CSCs were analysed by qPCR to determine whether they express the catalytic subunit of telomerase according to the method described in Example 2A. Tumour cell lines KG1 and MCF7 were used as positive controls and MSC from bone marrow (BM-MSC) as well as Human Diploid Fibroblast (HDF) was used as negative controls. mRNA was isolated as described in Example 2A, and expression of the catalytic subunit of telomerase was tested by qPCR using specific TaqMan probes. Expression of catalytic subunit of telomerase was not detected in CSCs (see FIG. 4A).

In addition, the telomerase activity in CSCs was compared to MSC or HDF by the Telomeric Repeat Amplification Protocol (TRAP), which is a highly sensitive assay based on the fluorometric detection and real time quantification of telomerase activity. Telomerase activity is temperature sensitive and it is inactivated at 85° C. The telomerase activity detected with or without incubation of samples at 85° C. was compared. Pellets of $1 \times 10^6$ CSCs were prepared and used for telomerase activity detection using the TRAPEZE RT Telomerase Detection kit (CHEMICON). CSCs from different donors and at different steps of in-vitro expansion (WCB and FP) were tested. The cells lines K562 and MCF7 were used as positive control samples. Telomerase activity was analysed following the instructions provided by manufacturer. PCR reactions were run on a StepOnePlus (Applied Biosystems). A standard curve with different amount of telomeric sequence was done and the telomerase activity quantification was analysed using the Quantification-Standard Curve software.

No significant activity was detected in any of the three cell types. In addition, a reduction in telomere length in CSCs during in-vitro cell expansion was detected, indicating that these cells do not elongate telomeres. This reduction in telomere length with each cell division will ultimately result in cessation of proliferation after extensive in vitro cell culture.

E. Senescence of CSCs After Extensive Expansion in Vitro

Figure 4:
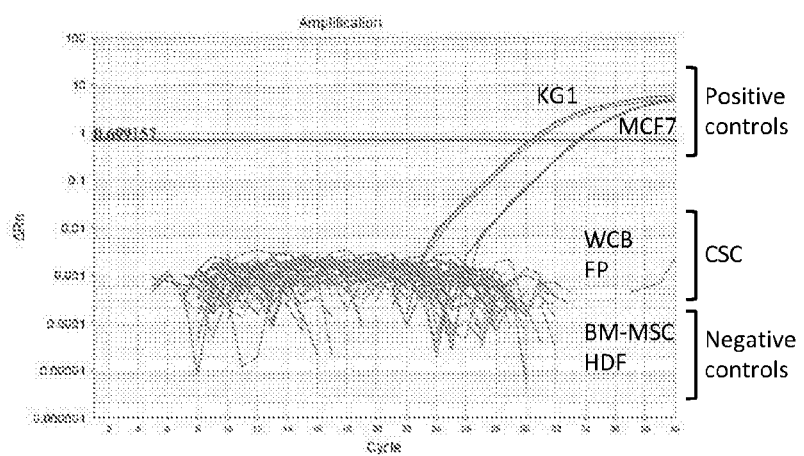
FIG. 4. A) CSCs do not express telomerase. No expression of the catalytic subunit of telomerase was observed by qPCR analysis on CSCs.
B) Telomeric Repeat Amplification Protocol (TRAP) telomerase activity in CSCs compared to MSC or HDF. No telomerase activity was observed in CSCs.
C) Cytochemical analysis of human CSCs after extensive expansion in-vitro (>30 population doublings) are made for detection of senescent associated β-galactosidase activity (SA-βGal). After in vitro expansion, some CSCs become blue when incubated with X-gal indicating that these cells are senescent.
Figure 4:
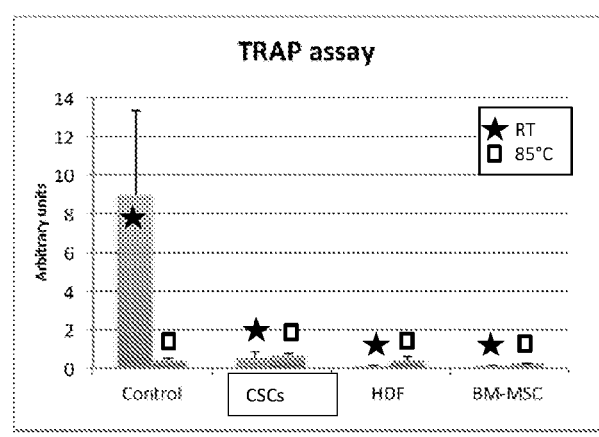
Figure 4:
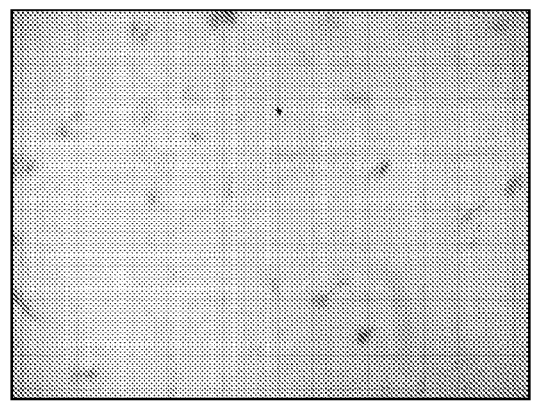

CSCs were cytochemically analysed to determine whether they become senescent after extensive (>30 population doublings) expansion in vitro. Senescence was detected based on senescence associated β-galactosidase activity (SA-βGal). CSCs were in-vitro expanded, fixed and incubated at pH 6 with the chromogenic substrate 5-bromo-4-chloro-3-indoyl β-D-galactopyranoside (X-gal), which yields an insoluble blue compound when cleaved by β-galactosidase. As shown in FIG. 4C, after in-vitro expansion some CSCs become blue when incubated with X-gal, thus indicating that these cells were senescent.

F. CSCs do Not Express Oct3/4 or Nanog

Figure 5:
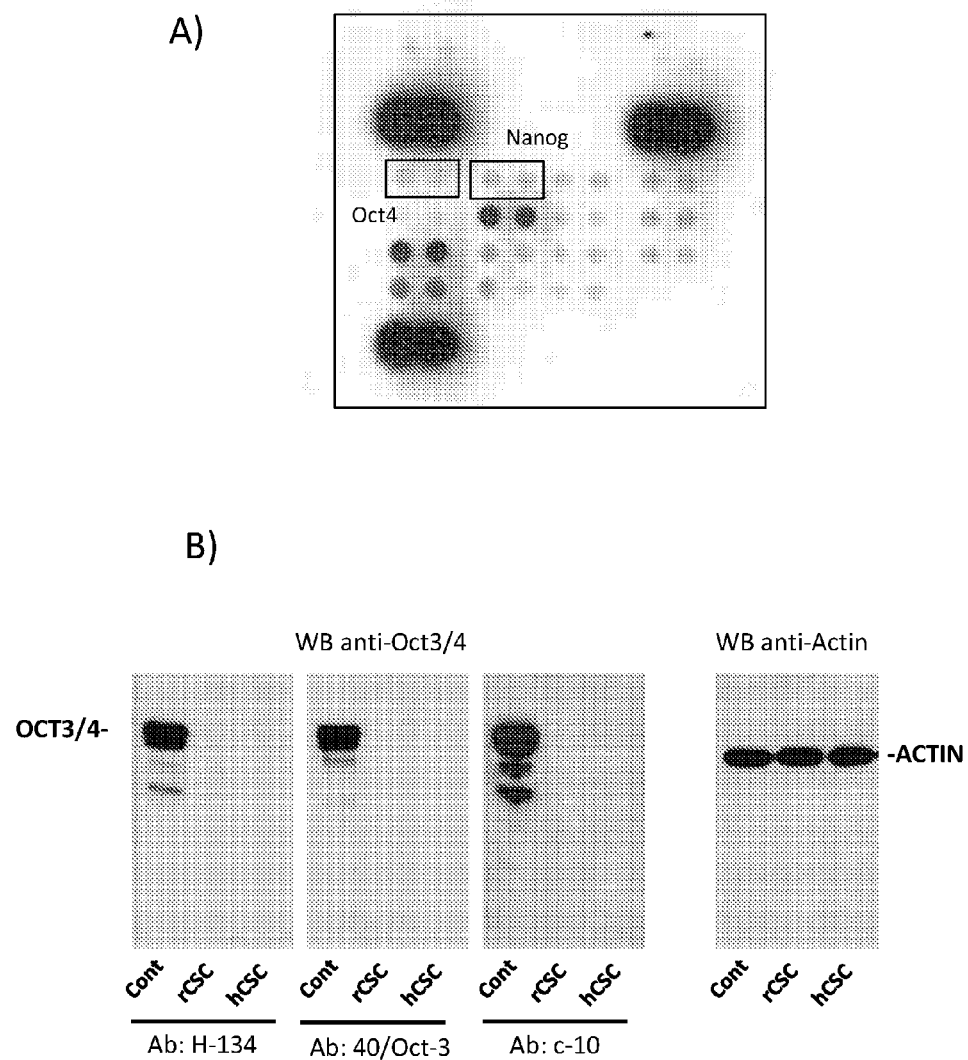
FIG. 5. A) CSCs do not express Oct3/4 or Nanog analysed by protein array.
B) CSCs do not express Oct3/4 or Nanog analysed western blot.

The expression of different genes implicated in stem cell development was analysed using a protein expression array as described above. As shown in FIG. 5A, no expression of Oct3/4 or Nanog was observed.

Oct3/4 expression was also analysed by Western Blot using three different antibodies in rat CSCs and in human CSCs. Cellular pellets of $1-5 \times 10^6$ cells were lysed in RIPA lysis buffer (20 mM Tris pH7.5, 150 mM NaCl, 2 mM EDTA, 1% Na-deoxicolate, 1% Triton X-100, 0.25% sodium dodecyl sulfate) complemented with a cocktail of protease inhibitors. Protein concentration of whole cell extracts (WCE) was determined using Nanodrop and equal amounts of WCE (50 μg) were loaded on a Tris-glycine gels and transferred onto a 0.45 μm polyvinylidene fluoride membrane (PVDF). Membranes were washed in Tris-buffered saline with Tween (10 mM Tris-HCl, pH 8, 150 mM NaCl, and 0.05% Tween 20), blocked 1 h at room temperature with 5% non-fat milk or 1% BSA in Tris-buffered saline with Tween, then probed over-night at 4° C. with the different primary antibodies at the concentrations recommended by the manufacturers. Immunoblots were treated with a HRP-conjugated secondary antibody followed by a luminescence reaction with ECL-plus. Equal loading was ensured by membrane re-probing with anti-β-actin antibody.

TABLE 5

Antibodies used for Western Blot analysis

| Target | Clone | Source |
|---|---|---|
| Anti-Oct4 | H-134 | Santa Cruz |
| Anti-Oct4 | C-10 | Santa Cruz |
| Anti-Oct4 | 40/Oct-3 | BD |
| Anti-Caspase 3 | 8G10 | Cell signaling |
| Anti-Actin | β-Actin | Cell signaling |

The NTERA cell line was used as a positive control. 50 μg of cell protein extract from CSCs was run on a SDS-PAGE gel, proteins were transferred to a nitrocellulose membrane and the presence of Oct3/4 was tested with specific antibodies (see Table 5). Actin was used as a loading control. As shown in FIG. 5B, the lack of Oct3/4 expression was confirmed by Western blot analysis.

G. WT1, HEY2, KDR, HHEX and HAND2 mRNA Expression is Higher in CSCs than in MSCs Expression of WT1, HEY2, KDR and HHEX in CSCs was compared with MSC from adipose tissue, using expression arrays according to the method described in Example 2A. As shown in Table 6, CSCs were found to express at least 20-fold more mRNA transcripts for WT1, HEY2, KDR and HHEX in CSCs than in MSCs obtained from adipose tissue.

TABLE 6

Comparative expression of WT1, HEY2, KDR and HHEX in CSCs and MSCs from adipose tissue

| Gene | Fold change | p-value |
| --- | --- | --- |
| KDR | 54.2 | 0.0312876 |
| HEY2 | 146.1 | 2.46E−04 |
| WT1 | 357.6 | 3.18E−04 |
| HHEX | 40.8 | 0.05 |

These results were confirmed by qPCR using specific TaqMan probes (see Example 2A). FIG. 17 summarises the qPCR analysis results, which show that GATA4, SOX17, WT1, HEY2, KDR, HHEX and HAND2 are over-expressed in CSCs when compared with MSCs used as reference cell line. The values in FIG. 17 are the Log 2 of the Relative Quantitation.

H. CSCs Overexpress the Secreted Factors IL-1α, CSF, PDGF and IL-1β

The comparative expression (fold change) of the secreted factors IL-1α, colony stimulating factor 3 (CSF3), PDGF and IL-1β was assessed in CSCs versus MSCs from adipose tissue by mRNA expression array. As shown in Table 7, the mRNA expression of the secreted factors IL1α, CSF, PDGF and IL-1β was at least 10-fold higher than in MSCs from adipose tissue.

TABLE 7

Comparative expressionof IL-1α, CSF3, PDGF and IL-1β in CSCs and MSCs from adipose tissue

| Gene | Fold change | p-value |
| --- | --- | --- |
| IL-1α | 69.2 | 0.05 |
| IL-1β | 12.7 | 0.001 |
| CSF3 | 32.3 | 0.025 |
| PDGFβ | 13.8 | 0.032 |

I. CSCs Secrete High Amounts of CCL2

The level of CCL2 secretion in the WCB and FB were determined by ELISA. CSCs were seeded at 5000 cells/cm$^2$ in DMEM/F12:Neurobasal medium (1:1) medium complemented with 10% serum. On the next day, the culture medium was replaced by media without fetal serum supplemented with growth factors Insulin-like Growth Factor 2 (IGF-II), basic Fibroblast Growth Factor (bFGF) and Epidermal Growth Factor (EGF). Supernatants from cell cultures were collected after 3 days, debris removed by centrifugation at 1500×g for 3 min and assayed immediately. Human CCL2/MCP-1 Quantikine ELISA kit (R&D systems) was used according to instructions of the manufacturer.

Figure 6:
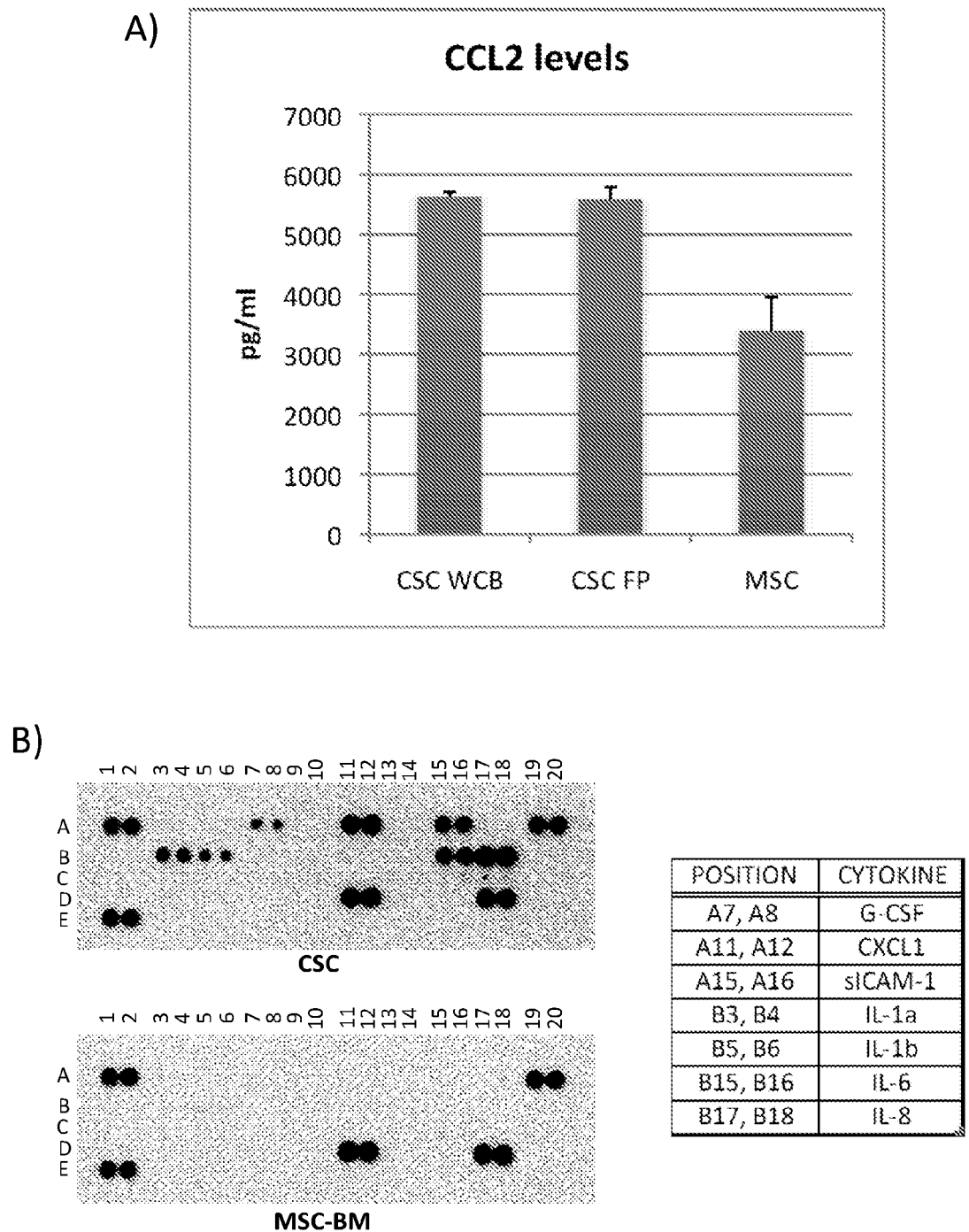
FIG. 6. A) ELISA studies have shown how CSCs express high amounts of CCL2 at Working Cell Bank and at Final Product (FP). MSC were used as reference cell line.
B) CSCs express IL-8, IL-6, CXCL6, sICAM1 and IL-1α proteins, as it can be observed in protein expression array studies.

As shown in FIG. 6A, CSCs express high amounts of CCL2 both in the WCB and at FP. In contrast, MSCs produced lower amounts of CCL2.

J. CSCs Overexpress IL-8, IL-6, CXCL1, sICAM1, IL-1α, IL-1β, G-CSF proteins

Protein array studies were performed in order to evaluate the level of expression of IL-8, IL-6, CXCL1, sICAM1, IL-1α, IL-1β and G-CSF proteins in CSCs. Mesenchymal stem cells from bone marrow (MSC-BM) were used as control cell line. An R&D human pluripotent stem cell antibody array was used. CSC lysates (200 μg of protein extract) were mixed with antibodies against protein related with stem cell regulation and then the protein-antibody complexes incubated with the membrane for protein quantification.

As shown in FIG. 6B, CSCs were found to express G-CSF, IL-8, IL-6, CXCL1, sICAM-1, IL-1β and IL-1α proteins at higher levels in CSCs than in MSCs.

K. CSCs do Not Express Nkx 2.5

Quantitative PCT (qPCR) was used to determine the levels of Nkx 2.5 expression in CSCs compared to bone marrow MSCs used as a reference cell line. mRNA was isolated from these cells, and the expression of Nkx 2.5 was assessed by qPCR using specific TaqMan probes. Expression of Nkx 2.5 was not detected in CSCs.

L. CSCs Express CD31 and CD49c Proteins but do Not Express CD133 or CXCR4 Proteins The expression of CD31, CD49c, CD133 and CXCR4 proteins was assessed by flow cytometry according to the method recited in Example 2C.

As in Example 2C, histograms of cell count vs intensity of fluorescence were obtained for each antibody staining, and cells were gated using forward versus side scatter parameters to eliminate debris. Gating analysis was applied when histograms corresponding to positive cells could clearly be differentiated from those obtained after isotype control and/or negative cells, in terms of levels of expression (intensity of fluorescence). For lower intensities of fluorescence, the number of positive cells was also confirmed by area subtraction of partially overlapping histograms resulting from binding of cells to both, marker specific and nonspecific isotype matched control antibodies. When area subtraction approach was used to quantify expression levels, cells were considered positive when having a expression greater than 30%.

The flow cytometry results in FIG. 3B indicate that CSCs do not express the chemokine receptor CXCR4 on its surface. CSCs are also negative for cKit (CD117) marker (as already stated, see FIG. 3A). Expression of these markers is negative, as the signal generated by the corresponding marker antibody has the same intensity as the signal generated by the isotype control. Similarly, no CD133 expression was detected by flow cytometry in the surface membrane of CSCs. As shown in FIG. 3B, the signal observed after incubation of CSCs with specific anti-CD133 antibody was similar to the one observed with control antibody (grey area).

CD31 is homogeneously expressed among the population of CSCs. It can be observed in FIG. 18 that the histogram generated by binding of CSCs to anti-CD31 antibody depicts a unique peak and a uniform distribution, showing increased intensity of fluorescence relative to the isotype control histogram (solid grey). That is, CSCs are positive for the CD31 cell surface marker. As shown in FIG. 18, expression of CD31 was higher than 30% when the area subtraction approach was used. CD49c was also shown to be homogeneously expressed in 100% of CSCs.

Example 3—Analysis of CSC Phenotypic Traits in Vitro

A. CSCs have a Low Immunogenicity Profile

The expression of the co-stimulatory molecules CD40, CD80 and CD86 and of MHC class I (or HLA class I) in CSCs was determined using the flow cytometric assay method described in Example 2C. CSCs were found to express MHC class I, but they do not express or express very low levels (<2%) of the co-stimulatory molecules CD40, CD80 and CD86.

B. The Morphology and Size of CSCs is Distinctive

Figure 7:
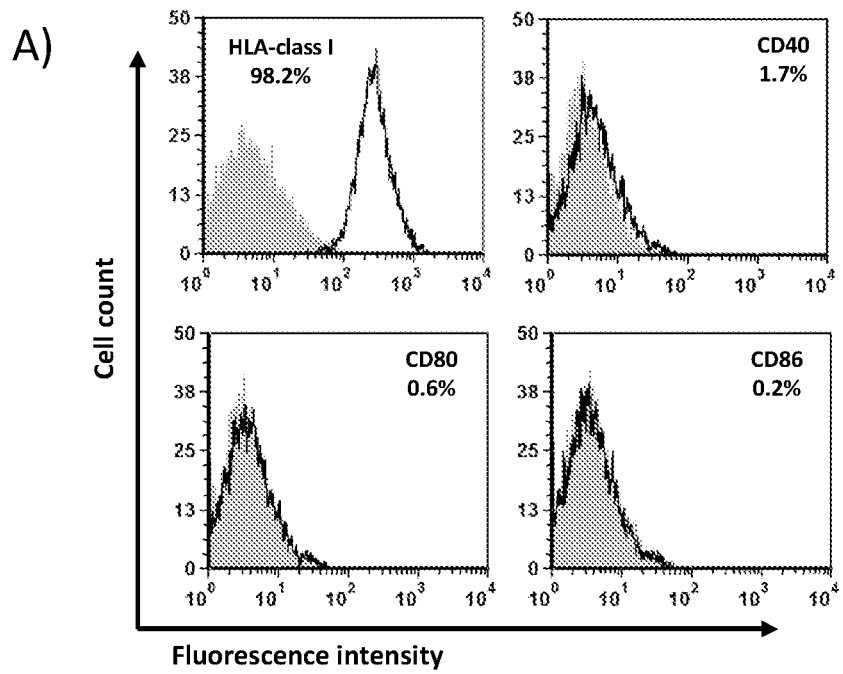
FIG. 7. CSCs express MHC class I but they do not express the co-stimulatory molecules CD40, CD80 and CD86.
Figure 8:
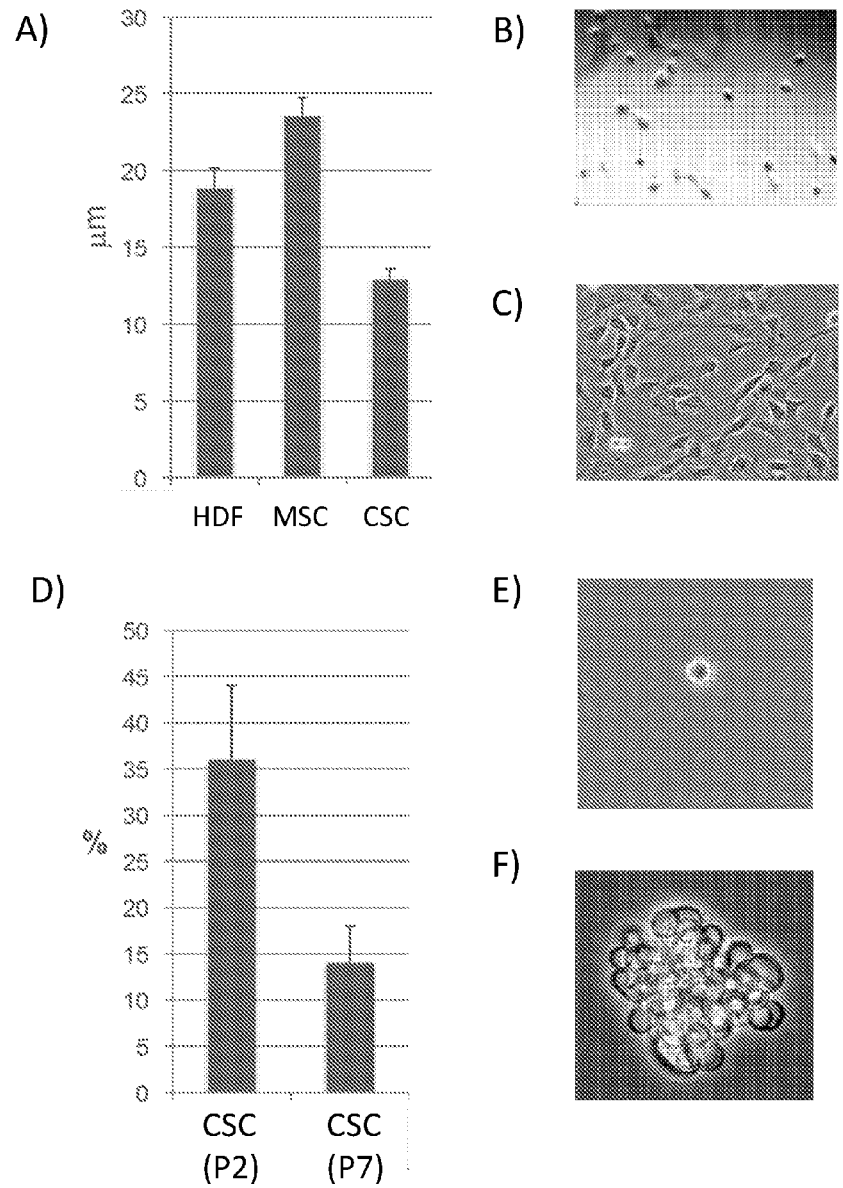
FIG. 8. A) CSCs cell size was analyzed after isolation and after in vitro expansion.
B) CSCs have a rounded morphology after isolation.
C) CSCs acquire a stromal-like morphology during in vitro expansion.
D) CSC have clonogenic capability at passage 2 (P2) and at passage 7 (P7).

The size of CSCs was analyzed after isolation and after in vitro expansion. The cell size was also measured in the final product after thawing the frozen cells. As shown in FIG. 8A, isolated CSC cells are smaller than MSCs and fibroblasts, and this smaller size is maintained after culturing. The average size of CSCs was below 15 μm of diameter and bigger than 10 μm as shown in FIG. 7.

As shown in FIG. 8B, CSC cells have a rounded morphology after isolation. The cells acquire a stromal-like morphology during in vitro expansion, as shown in FIG. 8C.

C. Clonogenic Capability and Ability of CSCs to Form Cardiospheres

The clonogenicity of CSCs was assessed at passage 2 (P2) and at passage 7 (P7) by seeding single cells in ultra low adherent 96-well plates wells. The presence of cardiospheres was analysed by visual inspection under the microscope at days 14 and 21 after seeding. As shown in FIG. 8D-F, CSCs were found to have clonogenic capability at passage 2 (P2) and at passage 7 (P7) and are able to form cardiospheres and to growth in suspension when seeded in ultra-low adherent plates.

D. CSCs are Able to Induce Monocyte Recruitment

Cell migration assays were performed to determine whether CSCs are able to induce the migration of monocytes across a porous membrane. 24-well migration chambers (Costar, USA) with 5 micron pore size inserts were used. MonoMac-1 cells were cultured at a suitable concentration so that they were in exponential phase at the time of the assay. The cells were counted, washed twice and placed in the inserts of the migration chamber ($2.5 \times 10^5$ cells in 100 μl). Conditioned media, which corresponded to the cell supernatants of CSCs, MSCs (from bone marrow) or HDFs, was placed in the lower part of the wells. The cells were incubated for 240 minutes at 37° C. with 5% $CO_2$. All the points were carried out in duplicate. The inserts were then removed and the cells that migrated to the lower part of the chamber were counted by means of flow cytometry. As shown in FIG. 9B, CSCs induce stronger monocyte recruitment when compared with MSC or HDF.

E. CSCs Demonstrate Immunoregulatory Capacity on Activated T Lymphocytes

The effect of CSCs on T cell immunoregulation was analyzed after labeling T cells with CFSE. HLA-mismatched CFSE-labeled PBMC ($1 \times 10^5$) were stimulated with Dynabeads Human T-Activator CD3/CD28 (Life Technologies) plus IL-2 (10 ng/ml) or with phytohaemagglutinin (PHA) in the absence or presence of mitomycin-C-treated CSCs ($1 \times 10^4$) for 5 days. At the end of co-cultures proliferation of T-cells was determined by flow cytometry, using CFSE tracking in CD3, CD4 or CD8 positive cells. As shown in FIG. 9C, CSCs demonstrate immunoregulatory capacity on activated T lymphocytes (CD3 positive).

F. Growth Factors Secreted by the CSC Promote Cell Survival

The cardioprotective capacity of factors secreted by CSCs on H9C2 myoblastic cells was studied in vitro by using CSC conditioned medium. Cell death of the H9C2 cells was induced using 1 mM hydroxide peroxide ($H_2O_2$), which causes the production of apoptosis-inducing oxygen free radicals. H9C2 cells were seeded at $20 \times 10^3$ cells/ml and 24 h later, 1 mM of $H_2O_2$ was added and cells incubated for a further 30 min. The growth medium was then replaced with conditioned culture medium from CSCs, MSCs-BM or HDFs and cells cultured for another 16 h. Finally, Alamar Blue was added (1:10 dilution) and 2 h later cell viability was analysed by quantifying absorbance at 570 nm in an EnVision multilabel Plate reader. As shown in FIG. 10A, addition of the CSC conditioned medium to H9c2 cells treated with hydrogen peroxide was found to prevent cell death and increase cell metabolism.

The pro-survival ability of the factors secreted by the CSCs was also assayed in H9c2 cells after serum deprivation. Serum deprivation apoptosis was induced by culturing cells for 24 h in serum-free medium. Upon initiation of the apoptotic program by serum deprivation, H9c2 cells activate caspase 3 by cleavage of the pro-form and caspase 3. Conditioned medium of CSCs, MSCs-BM or HDFs without fetal bovine serum was added and 24 h later activation of caspase 3 was analysed by Western Blot, according to the method described in Example 2F. As shown in FIG. 10B, pro-caspase3 activation was found to be reduced in starved H9c2 cells co-cultured in serum-free/CSC conditioned medium.

G. CSCs are Able to Differentiate into Various Lineages

The differentiation potential of CSCs to cardiac lineages was analyzed by immunofluorescence microscopy.

Human CSCs were plated at 5000 cells/cm$^2$ on 0.1% gelatin coated 6 wells plates and incubated in DMEM/F12 and Neurobasal (1:1) medium supplemented with 10% FBS ESCq, plus growth factors for 24 h. Cells were treated with 100 nM Oxytocin (Sigma-Aldrich) for three days and then trypsinized and seeded in p24 ultra-low adherent wells (Costar) (2000 cells/well). Seven days later, cardiospheres were harvested and distributed in 24 well plates, with laminin (Sigma-Aldrich) pre-coated glass slides (10 μg/ml), in differentiation media: α-MEM, FBS 2%, dexamethasone (1 μM) (Sigma-Aldrich), beta-glycerolphosphate (10 nM) (Sigma-Aldrich), ascorbic acid (50 μg/ml) (Sigma-Aldrich). During the first 4 days media was supplemented with TGF-β1 (5 ng/ml) (Peprotech), BMP-2 (10 ng/ml) (R&D systems, Madrid, Spain) and BMP-4 (10 ng/ml) (R&D systems) and then this supplement was replaced by DKK-1 (0.15 μg/ml) (Peprotech). At the end of the differentiation protocol (day 30) cells were analyzed by immunofluorescence microscopy. As shown in FIG. 11A-C, CSCs demonstrated expression of markers corresponding to smooth muscle, endothelial cells and cardiomyocytes after culture in specific differentiation medium.

CSCs were also able to differentiate to adipocytes and osteocytes after culturing in the appropriated medium. Adipocytic differentiation was analysed by oil red O staining and osteocytic differentiation confirmed by Alizarin red staining.

H. Genomic Stability of CSCs

Comparative genome hybridization analysis was performed to determine the genomic stability of isolated human CSCs and assess whether any chromosomal alterations, such as duplications or deletions, had occurred in CSCs after in vitro expansion. Oligo array-CGH analysis was performed using Human Genome CGH 44k microarrays (Agilent Technologies, Santa Clara, Calif., USA). A total of 1 µg of genomic DNA from the cells and a reference healthy genomic DNA (Promega, Madison, Wis., USA), were differentially labelled by random priming with Cy5-dCTP and Cy3-dUTP. The hybridization was carried out according to the manufacturer's protocol. Copy number altered regions were detected using ADM-2 (set as 6) statistics provided by AGW, with a minimum number of five consecutive probes, thus allowing the detection of any aberrant regions of at least 200 kb. FIG. 12 shows the comparative genome hybridization analysis for a human female genome. No chromosomal alterations were observed, thus demonstrating the stability of the genome of CSCs.

Example 4—Analysis of CSCs in Vivo

A. CSCs do Not Induce a Strong Humoral Response After Intracoronary Administration The immunogenicity of CSCs after intracoronary injection was assessed in pigs according to the timescale shown in FIG. 13A. $100 \times 10^6$ allogeneic pig CSC cells were administered by intracoronary injection into immunocompetent infarcted large white pigs and the presence of the allogeneic antibodies, IgG and IgM, against the injected cells was analysed before cell administration and at 15 and 30 days after cell administration. Thirty days after administration, $50 \times 10^6$ of the same CSCs were injected intravenously and the presence of specific alloantibodies in the serum was tested at day 3, 7, 15 and 30 after the second injection. The serum obtained from blood samples was incubated with the injected cells. The presence of alloreactive antibodies against the injected cells in the serum was analysed by flow cytometry using anti-IgG or anti-IgM labelled antibodies.

The presence of specific immunoreactive immunoglobulins (IgG and IgM) was analyzed in the different blood samples. It was not possible to find specific immunoreactive IgG against the injected cells during the first 30 days. On the contrary, after the second injection we observed the presence of CSC-specific Ig M and Ig G at days 7, 15 and 30, as shown in FIG. 13B. These results indicate that, although CSCs do not trigger a strong humoral response after administration, they are recognized and probably eliminated by the immune system generating an immunological memory that induce a stronger and faster response after a second administration.

B. Retention of CSCs After in Vivo Administration

The post-administration retention of CSCs in the heart CSCs was determined by tracing experiments. Human CSC were labeled with GFP and injected into the myocardium of immunodeficient rats 7 days after they were infarcted. The animals were sacrificed 24 hours after injection and the presence of GFP positive cells analyzed by histological analysis. Fluorescent-labeled microspheres were co-injected with the cells to be able to identify the site of administration. As shown in FIG. 14, these tracing experiments demonstrated that CSCs remains in the infarcted area for at least 24 h following injection.

C. CSCs Promote Cardio-Regeneration

The effect of CSCs on infarcted rat hearts was assessed by echocardiography and histological analysis. Immunodeficient nude rats of 200 to 250 g (HIH-Foxn1 mu, Charles River Laboratories, Inc., Wilmington, Mass.) were infarcted by permanent ligation of the anterior coronary descendent artery. Once the affected tissue acquired a pale colour, intramyocardical transplantation was performed (PBS or 5×105 CSC from different donors) at 2 points of the infarct border zone with a Hamilton syringe. At 15 days, 1 and 2 months after cell administration animals were sedated and cardiac function analysed by echocardiography.

Two months after implantation, animals were killed, hearts removed, washed with phosphate-buffered saline, fixed in 4% paraformaldehyde for 24 h and stored in 70% ethanol till further processing. Before inclusion, heart atriums were removed and the heart cut in three sections of similar size: apex region (A zone), medium region (B zone) where the ligation was done, and the region close to the valves (C zone). Every region was included in paraffin and three sections of 5 mm, spaced 75 mm from selected hearts (showed below), were dyed using Masson's Thrichrome stain technique. Histological analyses were performed and scar size, with respect to the total diameter of the left ventricle, was calculated. The percentage of muscular fibres with respect to the total wall thickness was calculated in a representative infarcted area. The CellA Olympus software was used to obtain histomorphometric measurements. Student's t test was used to analyse the significance of the data obtained by echocardiography or histological analysis.

As shown in FIG. 15A, significant higher cardiac function in animals injected with CSCs was observed when compared to control animals. In the cell-treated group, the improvement in cardiac performance in terms of Fractional Area Change (FAC) was observed 1 month after transplantation and maintained at 2 months. More specifically, two months after transplantation, FAC was 33.76±1.69% in saline and 42.53±8.29% in the CSC-treated group. The Anterior Wall Thickening (AWT) was significantly higher in animals transplanted with CSCs (18.93±4.18% in saline and 27.37±5.14% in CSC-treated group), indicating that CSCs are more effective at promoting new muscle formation and preventing remodelling than saline.

Histological analysis using Masson's tricromic stain also showed a significant reduction of the scar size and an increase in cardiomyocytes in the affected area, in rats treated with cells when compared to control animals. These experiments were done with CSCs obtained from four different donors to confirm the reproducibility of isolation and expansion process and to validate the bioequivalence between different batches.

D. CSCs do Not Cause Cardiac Toxicity Following Intracoronary Injection

In order to test the safety of administering CSCs, the presence of cardiac enzymes were monitored after injection of human CSC into healthy pigs. Administration solution (placebo) or doses of $50 \times 10^6$ human CSC were administered by intracoronary injection into the pigs. Cells were injected at a rate of 2 ml/min and, cardiac Troponin I (cTnI), Myoglobin and Creatin Kinase-MB, were quantified at before and 24 h after cell administration and no toxicity was observed. The results for cTnI are shown in FIG. 16.

E. CSCs do Not Cause Tumourigenesis

Two different experiments have been done in immunodeficient mice (SCID mice) for testing tumorogeneic potential of CSCs. CSCs were injected intravenous ($3 \times 10^6$ cells) or subcutaneous ($10 \times 10^6$ cells) in immunodeficient mice and the tumour formation analysed during 8 months or 4 months, respectively. All animals were subjected to a general clinical observation once per day (Monday to Friday) on a daily basis, as well as immediately after the test item administration, for the appearance of macroscopically visible adverse reaction to the test item administration. At the end of the experimental period, a full necropsy was carried out on each animal, and the abdominal, thoracic, cranial cavities, together with their associated organs were examined in situ.

Additionally, at the end of the experimental period, a histological evaluation of some organs was performed for each animal. The results of these studies (clinical observations, body and organ weights, necropsy observations and histological evaluation) demonstrate the lack of tumourigenesis of CSCs at the tested doses in SCID mice over the assayed period of time.

F. Justification for the Use of the Adult Cardiac Stem Cells of the Invention as a Therapeutic Product In Humans The cardio-protection, immunoregulatory capabilities and cardio-regenerative potential of the adult cardiac stem cells of the invention make them a suitable therapeutic tool for the treatment of different diseases such as ischemic heart disease, autoimmune diseases, wound healing processes or regenerative therapies. In particular, the following phenomenon mediated by the CSCs of the invention make them useful therapeutic tools for the treatment of diseases in which cell death or inflammatory process are involved:

The cardioprotective signals mediated by these cellular products (See FIG. 10) will limit the loss of cells after an insult.

The Immunoregulatory capabilities of CSCs will modulate the inflammatory process mediated by T cells and macrophages. Although the immune response at the initial stage after an insult is essential to remove cellular debris and initiate scar formation, a prolonged inflammatory process will not allow scar resolution and tissue regeneration.

Finally, in vivo experiments in a rat model showed the ability of CSCs for inducing the formation of new tissue, reducing the scar size and increasing the presence of new muscle fibres. This will be mediated by the ability of CSCs to activate endogenous stem cells.

Thus, all these activities mediated by CSCs make them useful therapeutic agents for the treatment of diseases in which cell death or inflammatory process are involved. In addition, these cells could be used for promoting tissue regeneration in pathologies where new tissue formation is required. In this sense, human ischemic heart disease could be treated using these cells. CSCs will limit cell loss during the acute phase of the disease, will modulate the inflammatory response to allow a faster regeneration and will finally activate endogenous tissue resident cells to promote the new tissue formation.

In addition, these cells can be administered at different moments of disease development. Cells can be administered during the acute phase of the disease to prevent cell loss and during the sub-acute or the chronic phase to modulate the immune response and to activate endogenous regeneration. The low immunogenic profile of the CSCs, as well as their immunomodulatory capabilities will prolong their survival in vivo and therefore increase their therapeutic potential.

The adult cardiac stem cells of the invention can be administered using different routes like intracoronary, intramyocardial, intravenous, intradermic, etc. The reduced size of CSCs compared to MSC make of these cells especially suitable for intracoronary administration. More than $30 \times 10^6$ cells can be intracoronary delivered without observing cTnI elevation.

Example 5—Example of a Clinical Protocol for the Intracoronary Infusion of Allogeneic Human CSCs in Patients with Acute Myocardial Infarction and Left Ventricular Dysfunction

| | |
|---|---|
| COMPOSITION | Active substance<br>$38 \pm 3 \times 10^6$ human cardiac stem cells (at the packaging time)<br>Primary (immediate) cell container::<br>Daikyo Crystal Zenith ® (CZ) vial of 2 ml capacity from Westpharma.<br>Excipients:<br>1:1 mixture of HypoThermosol ®-FRS (HTS-FRS) and CryoStor ® CS10 (DMSO 10%) from BioLife Solutions. The final DMSO concentration will be 5% and the final volume 1.8 mL.<br>Vehicle for injection:<br>Administration solution: Commercial HSA 5% diluted in saline solution (Octapharma ®).<br>The final product will be reconstituted directly in the administration syringe:<br>i. Administration solution, 16.2 mL<br>ii. Content of cell vial, 1.8 mL<br>Final volume in the syringe: 18 mL |
| ROUTE OF ADMINISTRATION | Intracoronary injection |
| INSTRUCTION FOR ADMINISTRATION | Product administration in infarct culprit vessel previously treated by primary PCI<br>4-7 days after primary PCI, up to 8 days from the onset of symptoms.<br>i. Fill the microaggregates filter with saline solution.<br>ii. Connect the administration syringe with the cell suspension to the filter and the catheter.<br>iii. Administer three boluses of 6 mL each (each bolus must last 3 minutes, manual control). A rest period of 3 minutes must be observed between each bolus. In total, the administration must last less than 30 minutes.<br>iv. Administration will be done using an over-the-wire infusion catheter with hydrophilic coating: 0.021"-0.023" diameter.<br>v. Administration of nitroglycerin during the procedure: 200-400 µg before each bolus.<br>vi. Administration of saline solution during the procedure: 1 mL after each bolus.<br>vii. Administration of heparin as recommended in European Guidelines |

The invention claimed is:

1. A method of preparing a substantially pure population of adult cardiac multipotent stem cells from cardiac muscle tissue comprising the steps of:
    (a) Preparing a suspension comprising cells from cardiac muscle tissue;

(b) Isolating a population of adult cardiac multipotent stem cells;
(c) Expanding said population of adult cardiac stem cells; and
(d) Selecting cells that express at least SOX17, GATA4, IL-1β and CD31; and which do not express the following markers: Oct4, Nanog, c-kit, Telomerase reverse transcriptase, CXCR4, CD133 and Nkx 2.5; and that are able to differentiate into at least all of the following cells types: adipocytes, osteocytes, endothelial cells and smooth muscle cells.

2. A method of preparing a substantially pure population of adult cardiac multipotent stem cells from cardiac muscle tissue comprising the steps of:
(a) Preparing a suspension comprising cells from cardiac muscle tissue;
(b) Isolating a population of adult cardiac multipotent stem cells;
(c) Expanding said population of adult cardiac stem cells;
(d) Preparing working cell banks (WCB) comprising a plurality of cell lines;
(e) Selecting cell lines from the working cell banks that express at least SOX17, GATA4, CD31 and IL-1β; and which do not express the following markers: Oct4, Nanog, c-kit, Telomerase reverse transcriptase, CXCR4, CD133 and Nkx 2.5; and that are able to differentiate into all of the following cells types: adipocytes, osteocytes, endothelial cells and smooth muscle cells;
(f) Expanding the selected cell lines; and
(g) Confirming the expression of at least SOX17, GATA4, CD31 and IL-1β; confirming the lack of expression of the following markers: Oct4, Nanog, c-kit, Telomerase reverse transcriptase, CXCR4, CD133 and Nkx 2.5; and confirming the ability to differentiate into all of the following cells types: adipocytes, osteocytes, endothelial cells and smooth muscle cells, in the final substantially pure population of adult cardiac multipotent stem cells.

3. The method of preparing a substantially pure population of adult cardiac multipotent stem cells of claim 1, wherein the selecting step comprises selecting cells that express WT1, HEY2, KDR, PDGF, CCL2, IL1α and/or CSF3.

4. A method of treating a subject suffering from a cardiovascular disease or ischemic injury comprising the step of administering to the subject: (a) an effective amount of isolated adult cardiac multipotent stem cells, wherein the adult cardiac multipotent stem cells express SOX17, GATA4, IL-1β and CD31, wherein the adult cardiac multipotent stem cells do not express Oct4, Nanog, c-kit, telomerase reverse transcriptase, CXCR4 protein, Nkx 2.5 and CD133 and wherein adult cardiac multipotent stem cells are able to differentiate into at least all of the following cell types: adipocytes, osteocytes, endothelial cells and smooth muscle cells; (b) an effective amount of a substantially pure population of the adult cardiac multipotent stem cells; or (c) a mixed population of cells comprising an effective amount of the adult cardiac multipotent stem cells wherein the mixed population also comprises cells other than the adult cardiac multipotent stem cells.

5. A method comprising administering to a subject: (a) an effective amount of isolated adult cardiac multipotent stem cells, wherein the adult cardiac multipotent stem cells express SOX17, GATA4, IL-1β and CD31, wherein the adult cardiac multipotent stem cells do not express Oct4, Nanog, c-kit, telomerase reverse transcriptase, CXCR4 protein, Nkx 2.5 and CD133 and wherein the adult cardiac multipotent stem cells are able to differentiate into at least all of the following cell types: adipocytes, osteocytes, endothelial cells and smooth muscle cells; (b) an effective amount of a substantially pure population of the adult cardiac multipotent stem cells; or (c) a mixed population of cells comprising an effective amount of the adult cardiac multipotent stem cells wherein the mixed population also comprises cells other than the adult cardiac multipotent stem cells, wherein
the adult cardiac multipotent stem cells induce cardiac tissue repair by one or more of the following mechanisms:
(1) recruitment of monocytes;
(2) immunomodulation;
(3) activation of angiogenesis;
(4) promoting cardio-regeneration and/or
(5) inducing regeneration of endogenous cardiomyocytes.

6. A method comprising administering to a subject: (a) an effective amount of isolated adult cardiac multipotent stem cells, wherein the adult cardiac multipotent stem cells express SOX17, GATA4, IL-1β and CD31, wherein the adult cardiac multipotent stem cells do not express Oct4, Nanog, c-kit, telomerase reverse transcriptase, CXCR4 protein, Nkx 2.5 and CD133 and wherein the adult cardiac multipotent stem cells are able to differentiate into at least all of the following cell types: adipocytes, osteocytes, endothelial cells and smooth muscle cells; (b) an effective amount of a substantially pure population of the adult cardiac multipotent stem cells; or (c) a mixed population of cells comprising an effective amount of the adult cardiac multipotent stem cells wherein the mixed population also comprises cells other than the adult cardiac multipotent stem cells, wherein the method:
(a) treats autoimmune diseases, inflammatory process and/or chronic ulcers;
(b) promotes wound healing in the subject; or
(c) prevents allogeneic organ transplant rejection in the subject.

7. The method of claim 4, wherein the method comprises regenerating cardiac tissue in the subject.

8. The method of claim 4, wherein the method comprises treating acute myocardial infarction in the subject, and wherein the adult cardiac multipotent stem cells; the substantially pure population of adult cardiac multipotent stem cells; or the mixed population of cells are administered via the intracoronary route; and wherein the dosage of said adult cardiac multipotent stem cells is from $1 \times 10^6$ to $50 \times 10^6$ cells.

9. The method of claim 5, wherein the adult cardiac multipotent stem cells, substantially pure population or mixed population are administered intravenously, intra-arterially, intracoronarily or intramyocardially.

10. The method of claim 5, wherein the adult cardiac multipotent stem cells, substantially pure population or mixed population are administered at a dose of $1 \times 10^6$ to $50 \times 10^6$ cells.

11. The method of claim 10, wherein the adult cardiac multipotent stem cells, substantially pure population or mixed population are administered at a dose of $25 \times 10^6$ to $45 \times 10^6$ cells.

12. The method of claim 11, wherein the adult cardiac multipotent stem cells, substantially pure population or mixed population are administered at a dose of $35 \times 10^6$ to $40 \times 10^6$ cells.

13. The method of claim 8, wherein the adult cardiac multipotent stem cells, substantially pure population or mixed population are administered at a dose of $25\times10^6$ to $45\times10^6$ cells.

14. The method of claim 13, wherein the adult cardiac multipotent stem cells, substantially pure population or mixed population are administered at a dose of $35\times10^6$ to $40\times10^6$ cells.

15. The method of claim 5, wherein the adult cardiac multipotent stem cells are allogeneic to the subject.

16. The method of claim 4, wherein the cardiovascular disease is selected from the group consisting of: myocardial infarction, chronic ischemic cardiomyopathy, cardiomyopathy and chronic heart failure.

17. The method of claim 4, wherein the adult cardiac multipotent stem cells are isolated from cardiac tissue using immunoselection with one or more immunoselective antibodies.

18. The method of claim 17, wherein the cells are immunodepleted for CD45 positive cells and immunoselected for c-kit positive cells.

19. The method of claim 4, wherein the adult cardiac multipotent stem cells:
(a) further express CD49c and HHEX;
(b) are isolated from heart muscle tissue;
(c) express one or more of the following markers: KDR, HEY2, WT1, CCL2, IL-1α, CSF3, PDGF-13, CD166, CD105, CD90, CD44, CD29, HAND2, MHC class I and/or IL-8;
(d) do not express one or more of the following markers: CD45, CD34, CD11b, CD40, CD80 and/or CD86; and/or
(e) have a diameter of ≤ about 10 μm to ≤ about 15 μm.

20. The method of claim 4, wherein the adult cardiac multipotent stem cells are:
(a) able to form spheres when cultured in suspension;
(b) able to induce monocyte recruitment;
(c) able to modulate a T lymphocyte response;
(d) able to secrete anti-apoptotic factors; and/or
(e) able to form clones.

21. The method of claim 4, wherein the substantially pure population of adult cardiac multipotent stem cells is isolated from cardiac muscle tissue, comprising the steps of:
(a) preparing a suspension comprising cells from cardiac muscle tissue;
(b) isolating a population of adult cardiac multipotent stem cells;
(c) expanding the population of adult cardiac multipotent stem cells; and
(d) selecting cells that express at least SOX17, GATA4, IL-1β and CD31; and which do not express the following markers: Oct4, Nanog, c-kit, Telomerase reverse transcriptase, CXCR4, CD133 and Nkx 2.5; and that are able to differentiate into at least all of the following cells types: adipocytes, osteocytes, endothelial cells and smooth muscle cells.

22. The method of claim 21, wherein the selecting step comprises selecting cells that express WT1, HEY2, KDR, PDGF, CCL2, IL 1α and/or CSF3.

* * * * *